US011566985B1

(12) United States Patent
Gupta

(10) Patent No.: US 11,566,985 B1
(45) Date of Patent: Jan. 31, 2023

(54) EXPANDABLE JACKETS FOR PRESSUREMETER PROBES FOR MAINTAINING UNIFORM RADIAL EXPANSION OF SOILS FOR DETERMINING STRESS-STRAIN RELATIONSHIP IN SUBSURFACE SOILS, INTERMEDIATE GEOMATERIALS AND ROCK

(71) Applicant: Ramesh Chandra Gupta, Ashburn, VA (US)

(72) Inventor: Ramesh Chandra Gupta, Ashburn, VA (US)

( * ) Notice: Subject to any disclaimer, the term of this patent is extended or adjusted under 35 U.S.C. 154(b) by 0 days.

(21) Appl. No.: 17/714,368

(22) Filed: Apr. 6, 2022

(51) Int. Cl.
*G01N 3/10* (2006.01)
*G01N 33/24* (2006.01)
*G01N 3/08* (2006.01)

(52) U.S. Cl.
CPC ............... *G01N 3/10* (2013.01); *G01N 3/08* (2013.01); *G01N 33/24* (2013.01); *G01N 2203/025* (2013.01); *G01N 2203/0266* (2013.01)

(58) Field of Classification Search
CPC ................................ G01N 3/10; G01N 33/24
See application file for complete search history.

(56) References Cited

U.S. PATENT DOCUMENTS

| 9,383,346 B2 | 7/2016 | Gupta | |
|---|---|---|---|
| 9,546,940 B2 | 1/2017 | Gupta | |
| 10,060,898 B2 | 8/2018 | Gupta | |
| 2018/0120283 A1* | 5/2018 | Gupta | .................... G01N 33/24 |

OTHER PUBLICATIONS

Cambridge INSITU Ltd. (2011), "pressuremeter Testing in Ruritania", www. Cambridge-insitu.com, Cambridge, UK.
Hustulid, W.A. (1976). "An analysis of the Goodman Jack", The 17th U.S. Symposium on Rock Mechanics, Snowbird, Utah.
In Situ Site Investigation. "High Pressure Dilatometer (HPD)", www.insiyusi.com, ESusex, UK, 2017.
Slope Indicator Company (2010). "Introduction and Specifications for Goodman Jack", www.slopeindicator.com, Stone Mountain, GA 30087.
RocTest (2014). Instruction Manual forSelf-Boring Pressuremeter, Model: BOREMAC, www.roctest-group.com, Canada.
RocTest (2014). "Texas A&M Pressuremeter, Instruction Manual", www.telemac.com, Canada, USA.

* cited by examiner

*Primary Examiner* — Paul M. West

(57) ABSTRACT

Expandable Jacket surrounding a pressuremeter probe prevents barrel shape to form and maintains cylindrical shape with uniform radial displacement throughout its height, removing shortcomings of the existing pressuremeters. For the pressuremeter probe to determine horizontal stress versus plane strain relationship in soils and intermediate geomaterials, an expandable comprises of one layer of circular arch shaped segmented plates surrounded by flexible bands or rings. The expandable jacket surrounds a membrane which itself surrounds a porous tube with holes. Borehole less than the diameter of probe is drilled either by pre-boring or self-boring and then pushing the probe with cutter ring. For the pressuremeter probe to determine horizontal stress versus plane lateral strain relationship for rocks, the expandable jacket comprises of two layers of the circular arch shaped segmented plates surrounded by flexible bands or rings and first layer surrounding a plurality of pistons, and second layer surrounding the first layer.

10 Claims, 11 Drawing Sheets

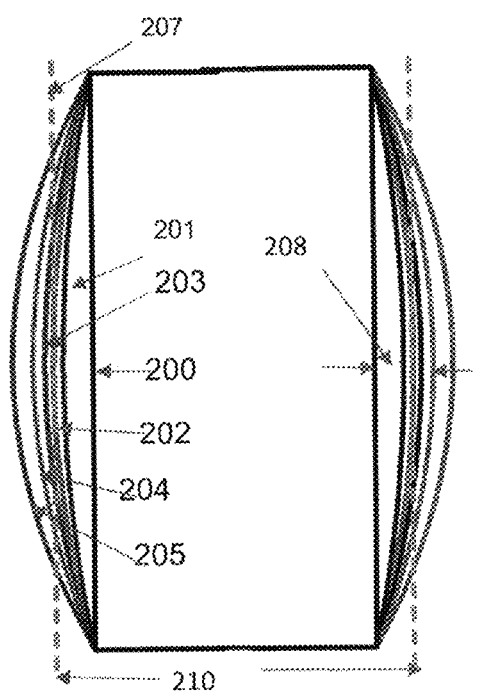
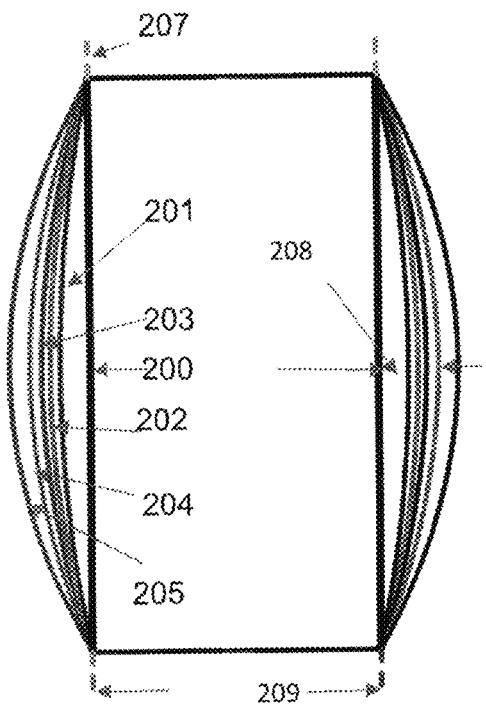
FIG. 1A  FIG. 1B
| Table 1A: Texas A & M Probe ||||| Table 1A: SBPMT Probe ||||
|---|---|---|---|---|---|---|---|---|
| Radius of Probe | Barrel Shape No. | Increase in radius at mid-height in % | Radius of Test Hole | | Radius of Probe | Barrel Shape No. | Increase in radius at mid-height in % | Radius of Probe = Radius of Test Hole |
| r | 201 | 7.81 | 1.1 r | | r | 201 | 7.81 | r |
| r | 202 | 10.42 | 1.1 r | | r | 202 | 10.42 | r |
| r | 203 | 12.51 | 1.1 r | | r | 203 | 12.51 | r |
| r | 204 | 15.64 | 1.1 r | | r | 204 | 15.64 | r |
| r | 205 | 20.87 | 1.1 r | | r | 205 | 20.87 | r |

# EXPANDABLE JACKETS FOR PRESSUREMETER PROBES FOR MAINTAINING UNIFORM RADIAL EXPANSION OF SOILS FOR DETERMINING STRESS-STRAIN RELATIONSHIP IN SUBSURFACE SOILS, INTERMEDIATE GEOMATERIALS AND ROCK

TECHNICAL FIELD

This application is for applying for a utility patent in the technical field which includes civil engineering and geotechnical engineering testing. This specification/description is complete-in-itself. This invention is not sponsored or supported by federally sponsored research or development. This invention has been developed by me, Dr. Ramesh Chandra Gupta, Ph. D., P. E, President and Sole Owner of SAR6 INC., solely at my own cost and time. There is no joint research agreement with anyone. It is my individual research work. The inventor, Dr. Ramesh Chandra Gupta is a Citizen of the United States of America.

BACKGROUND OF INVENTION

For this invention, an expandable jacket has been used primarily to maintain a uniform radial expansion of a Pressuremeter Probe in horizontal and radial directions to maintain its cylindrical shape throughout its height at any instant of time during the test. Thus, the soil or intermediate geomaterials or rock (as case may be), in the test depth equal to the height of the probe, experiences uniform radial expansion to provide uniform area of cross-section of the expanding probe and lateral horizontal stress and lateral strain, to theoretically calculate their modulus of deformation and other engineering properties of soils, correctly, using plane strain-horizontal relationship. The details of the expandable jacket for pressuremeter probes for soils and intermediate geomaterials and rock is not the same but different in the sense, expandable jacket for pressuremeter for soils and intermediate geomaterials uses only one layer of circular arch shaped segmented plates surrounding the membrane. Whereas, the expandable jacket for pressuremeter probes for rocks uses two layers of circular arch shaped segmented plates, on the first layer of circular arch shaped segmented plates, hydraulic jacks apply load on each circular-arch segmented plate, and while the second layer of circular-arch segmented plate surrounds and staggered over the first layer of the circular-shaped segmented plates to equally distribute horizontal load. The second layer of circular arch shaped plates surrounds and is in contact with the full circumference of the test hole in the rock from the beginning of the test. Similarly, the single layer of the circular-arch shaped plates of the expandable jacket for the pressuremeter probe for soils and intermediate geomaterials, surrounds and in contact with the full circumference of the test hole.

The preparation of test holes in soils and intermediate geomaterials uses different methods. In the first method, a borehole equal to the diameter of the pressuremeter probe is drilled and then the pressuremeter probe under vertically applied downward force of the drill rig is pushed to the test depth. In the second method, the borehole equal to the diameter of the probe is drilled up to top of the test depth, and then the borehole less than the diameter of the probe is drilled from the top of test depth to depths some distance below the bottom of the test depth. Thereafter, the pressuremeter probe is pushed to seat bottom of the pressuremeter probe at the bottom of the test depth, under the downward vertical forces taking reaction from CPT Truck/Rig, or drill rig with or without soil anchors or moveable loaded box/platform or loaded box/platform with or without soil anchors. The cutting rings at the bottom of the pressuremeter probe scraps/cuts the soil which drops in the hole below the pressuremeter probe. The loading system could change from project site to project site, depending on availability of equipment and site accessibility. After completion of the test, the pressuremeter probe is pulled out of the ground and same procedure is repeated to perform another test. In the third method, it is not necessary to pull the probe out of the ground after completion of the test, because the borehole is drilled by self-boring method to bore the hole to a diameter less than that of the probe, and then pushing the probe under the downward vertical forces taking reaction from CPT Truck/Rig, or drill rig with or without soil anchors or moveable loaded box/platform or loaded box/platform with or without soil anchors, cutting/scraping the borehole wall without disturbing the in-situ soil. Second and third methods shall prepare test holes with almost no disturbance to soil surrounding the test hole.

The description of structural components of existing pressuremeter probes, drilling methods and their shortcomings with technical problems are explained Section 4(a). Solution of the technical problems and shortcomings and how the expandable jacket surrounding the pressuremeter probes described in this application will solve the shortcoming and technical problems are also explained in Section 4(a), which then have been summarized in Section 4(b). The detailed description of pressuremeter probes using expandable jacket has been explained in Section 6.

SUMMARY OF INVENTION (a) Technical Problem with Existing Pressuremeter Test Probes (i) Menard Pressuremeter Test and Texas A & M Pressuremeter Test Lois-Francois-Augus Nenard (1960) received a French Patent FR794886A for the invention entitled "Device for studying the deformation under load of a homogeneous medium". The pressuremeter consists of two parts, the readout unit, which rests on the ground surface and the probe that is inserted into the borehole, the diameter of which is about 5 to 15% larger than the diameter of the probe. The probe consists of three independent cells, a measuring cell and two guard cells (one above and other below the measuring cell). Once the probe is at the test depth, the guard cells are inflated to brace the probe in place. Then the measuring cell is pressurized with water, inflating its flexible rubber bladder, which exerts a pressure on the borehole wall. As the pressure in measuring cell increases, the borehole walls deform. The pressure within the measuring cell is held constant and the increase in volume required to maintain the constant pressure is recorded. The probe comes with a control unit which houses all the regulators and valves required to reduce and control the pressure applied to the probe cells. It also contains a reservoir which supplies the flow of water to the measuring cell. The volume variations during a test are read on a sight tube. The readings are taken at 15, 30 and 60 seconds The Texas A & M Pressuremeter probe is similar to the Menard Pressuremeter probe, except that the guard cells have been eliminated, but the length of the measuring cell has been increased to limit the end effect. The method of applying pressure and measuring the increase in volume during the test is different. The membrane is fixed at the ends. It consists of a control unit which contains a mechanical actuator which has cylinder, a piston, connectors, sensors and a valve. The actuator has four support columns and two crank handles. Like the Menard Pressuremeter probe, the Texas A & M Pressuremeter probe is placed in a borehole which is 5 to 15% larger than that of its probe. The membrane is protected by a Chinese lantern consisting of thin aluminum/stainless steel vertical strips surrounding the membrane and fixed at the ends along with the membrane.

Since the diameter of the borehole is larger than the diameters of the both the above-mentioned probes (200), its flexible rubber membrane when inflated will not immediately touch the borehole wall but only after elapse of sometime during the test as Shown in FIG. 1A. During continued expansion of the probe, it will form barrel shape (201) and sometime later, the barrel shape (203) will touch the borehole wall (207) only at the mid-height of the probe, when the diameter of barrel shape at mid-height of the probe becomes equal to bore hole diameter (210), as shown in FIG. 1A. When further inflated under increase in applied pressure, the central part of the rubber membrane will dig in the borehole soil wall, as shown by Barrel shapes (204 and 205). Since the surface of the flexible rubber membrane becomes hard or rather incompressible, because of containing incompressible pressurized water locked in for 15 to 60 seconds, the membrane will maintain circular arch shape or barrel shape, whether inflated in air or whether inflated in the borehole of the in-situ soil with very soft or soft or stiff or perhaps even in hard or dense soil, as shown in FIG. 1A. The modulus of pressurized water filled in the barrel shape probe is many times more than that of even hard and dense soil. The difference between the radius of the circular arch of the barrel shape and the perpendicular distance from the chord to the circular arch center (208) may reduce somewhat if the soil behind the borehole wall is hard or dense, but reduced barrel shape shall still be maintained, because the membrane's two ends are fixed and it can only inflate by forming the barrel shape. Therefore, above-mentioned two probes do not expand with uniform radial expansion throughout its height. Although, this pressuremeter test is assumed to be performing a plane strain test, it is not so, as is clear from the barrel shapes shown in FIG. 1B. The radial expansion is zero at the ends and gradually increasing to maximum at the mid-height and then again gradually reducing zero on the opposite end. Therefore, even though applied pressure throughout the probe height is equal but radial expansion through the height is varying and not equal. Assuming the area of cross-section of the probe as average cross-section and calculating radial displacement as an average over the height and then comparing with applied horizontal stress provides incorrect relationship. There are no upper and lower guard cells in Texas A & M PMT, therefore decompression of soil takes place in an open borehole below and above its probe. All these shortcomings of the above two mentioned pressuremeter probes are overcome by my invention as described in my application by using an expandable jacket around the membrane to control a uniform radial expansion throughout its height.

(ii) Self-Boring Pressuremeter Probe (SBPMT)

The self-boring pressuremeter (SBPMT) was developed at the University of Cambridge (Wroth and Hughes, 1973). The probe is about 83 mm (3.26 inches) in diameter and 1.2 m (3.94 ft) long. Approximately 0.5 m is the expandable section and is expanded by dry nitrogen or compressed air. A typical test will expand the instrument by 10%. The membrane covering the expanding portion of the instrument is in two parts. The inner layer which is sealed is made of polyurethane and is about 1.25 mm thick. This inner membrane is covered by an outer layer, which is made up of stainless-steel strips bonded to a thin rubber membrane to protect any inclusions that might puncture the inner membrane. It is a costly device, with a complex and time-consuming operation, requiring highly specialized staff for its operation. The SBPMT provides an estimate of the stress state, stiffness, and strength parameters with possibility of estimating the at-rest horizontal stresses and the coefficient of earth pressure at rest. The SBPMT is self-boring, that is, it is capable of opening a borehole by its own means with removal of soil as it penetrates the soil mass. At the test depth, by means of internal compressed air pressure, the membrane is forced to expand and the radial deformation is measured by three transducers arranged at mid-height of the membrane at circumferentially spaced points of 120°. The upper and lower rigid parts of the probe avoid decompression of the surrounding soil above and below the cylindrical area surrounded by the rubber membrane. Total pressure transducer, and pore water pressure cell measure the total internal pressure while the pore water transducer measures pore water pressures as it increases during the test. Because of the complexities of SBPMT, this probe is rarely used in the United States, and because of its simplicity, engineers generally use Texas A&M or Menard Pressuremeter.

French SBPMT, developed about at the same time as Cambridge SBPMT has about the same components and functions similarly. BOREMAC model of SBPMT has been developed by ROCTEST. It is 68 mm in diameter and 126 mm in length with a threaded cutting shoe. The rigid upper and lower pieces are attached flush with an intermediate cylindrical part which is surrounded by expandable rubber membrane. The Chinese lantern has been replaced by a second membrane covering the first membrane.

The SBPMTs shall also form a barrel shape as shown in FIG. 1B, whether inflated in air for calibration of the membrane or in a borehole which is of the same diameter (209) as that of SBPMT probe (200, 210). In SBPMT, the expandable membrane touches the borehole walls from the beginning and exerts pressure on the in-situ soil to radially displace the soil throughout its height from the beginning of the test, but forms a barrel shape, because (1) the membrane is fixed at the ends, (2) the inflated and pressurized membrane becomes very hard, and is much harder than most in-situ soil, even harder than hard or dense soils, and (3) therefore the inflated and pressurized membrane shall dig in the in-situ soil to displace the soil to form a barrel shape as shown by curves (201 through 205). The modulus of elasticity of the hard barrel shape of SBPMT probe locked in gas pressure shall be much greater than that of even the hard soils. Football players know the effect when a pressurized air-filled football hits their heads, even though gas pressure in football is much lower than what is applied in SBPMT during the test. Therefore, the radius of the borehole/membrane at the mid-height at any instant of time is of the maximum value and its value reduces gradually towards lower and upper ends, similarly as explained for Texas A&M and Menards pressuremeter probes in Section 4(i). The membranes do not possess isotropic properties, because of this reason, generally each of the three displacement transducers, positioned only at mid-height and spaced circumferentially at 120° provide different values of radial displacement during the test (Cambridge Insitu Ltd., 2001). An average value from the readings of three transducers is calculated. Therefore, lateral pressure versus radial displacement relationship is representative only at the mid-height and not throughout the height and does not represent lateral pressure versus plane strain relationship throughout the height of the SBPMT. Therefore, assumption of plane strain although assumed for theoretical calculations and determining engineering properties accordingly may not be providing accurate values. The pressuremeter probe using an expandable jacket in this application shall reduce the influence of the expandable membrane and therefore should be expected to inflate the expandable jacket and probe uniformly to provide plane strain condition all along its height. Thus, this shortcoming of SBPMTs shall also be overcome by my invention.

The pressuremeter probes described in this application require pre-boring to the top of test depth where the top of the probe shall be situated for performing the test and then boring to a diameter less than the diameter of the probe, up to and below the test depth. None of these drilling operations will require special skill other than what drill operators possess. When the probe has been seated as above, the probe is pushed under downward vertical force exerted by drill rig or CPT rig or a moveable box, and the soil being cut by cylindrical shaped cutter ring to a diameter equal to that of the probe. This operation shall provide good quality of borehole with almost no disturbance of the soil. The cut soil shall fall in the borehole below the probe and therefore, no soil shall be pushed into the in-situ soil to disturb it.

Menard PMT or Texas A&M PMT cannot be pushed in a borehole of diameter equal to that of the probe, that is why a borehole 5 to 15% larger than the diameter of the probe is required, but the pressuremeter probe surrounded by the expandable jacket and provided with sufficiently thick porous tube (as specified in my application) designed to push in a hole equal or slightly less than the diameter of the probe shall provide reasonably accurate data.

(iii) High Pressure Dilatometer

High pressure dilatometer (HPD) is designed to perform in-situ load-displacement tests to determine strength and stiffness properties of the ground in radially horizontal direction, primarily for rock, but can also be used for testing stiff clay and cemented sand. The HPD is inserted into a borehole formed by conventional drilling methods. It also comprises a cylindrical probe covered by a flexible membrane that is expanded against the ground by oil or gas. Measurements are made internally by radial displacement strain arms and pressure cells, with digital data transmitted to the surface via an umbilical cable. Maximum working pressure is limited to 20 MPa (2900 psi). When inflated in stiff clay and cemented sand, the membrane will form a barrel shape losing its initial cylindrical shape as happens in Menard or Texas A&M pressuremeter or SBPMT. Maximum working pressure of 20 MPa (2900 psi) is too low for testing rocks to get anywhere close to even 30% of the peak stress.

(iv) Goodman Jack

The Goodman Jack (www.slopeindicator.com, Goodman et. al., 1968) is coupled to the drill rod and inserted into the borehole, along with its hydraulic lines and signal cable. When the jack is in position, a hand pump is used to activate the pistons within the jack. The pistons push two curved bearing plates, each of 90° circular arcs, 1.5" radius, diametrically opposite to each other, producing a uniform uniaxial-stress field in the direction against each other. The two curved bearing plates positioned in directionally opposite directions with a gap of uncovered circular 90° arcs of rock in between them, apply horizontal forces to the borehole in opposite directions and create forces to separate rock mass in directionally opposite directions. The circular arc plate separation is measured (using two LVDTs) along the direction of the ram axis as a function of the applied stress to plot a curve. To compute the apparent modulus of elasticity from the curve (Heuze, 1984, 1985), one uses equations developed from elastic theory along with some assumptions. Then Hustruild correction (Hustruild, 1976) is applied on the value of the apparent modulus of elasticity to obtain true modulus of deformation. Based on further research, the two factors may lead to a lower value of true modulus of deformation, one was non-full rock/platen contact when the borehole is undersized or oversized, and the other is the upper limitation of the applied hydraulic when used pressure. Goodman Jack can apply maximum hydraulic pressure of 69 MPa (9300 psi).

The pressuremeter probes for performing tests in rock as presented in this application uses a plurality number of loading circular arch shaped segmented plates covering the full circumferential area of the borehole and to apply equally distributed load on the full circumference of the borehole in the rock. For this purpose, the pressuremeter probe uses two layers of circular arch shaped segmented plates staggered over each other. A plurality of pistons on a horizontal plane and then vertically spaced several heights within the probe are used to apply horizontal load to the full circumferential area of the bore hole in the test height to determine modulus of elasticity. In this way much higher stress can be applied on rock on the full area of the borehole to provide reasonably accurate modulus of deformation of rock.

(a) Solution to Problem and Advantageous Effects of Invention

In Section 4(a) (i-iv), several types of pressuremeter probes in use in the industry have been discussed with their short comings. It must be stated that there are many models of pressuremeters manufactured by various organizations, but all are based on the same principles using membrane or hydraulic jacks. In this section at the end of discussion for each pressuremeter, it has been explained how these shortcomings shall be overcome by the invention explained in this application. The advantageous effects of this invention shall be determination of accurate in-situ engineering properties of soils, intermediate geomaterials and rock.

BRIEF DESCRIPTION OF THE SEVERAL VIEWS OF THE DRAWING

FIG. 1A: Calculated Inflation curves for Menard and Texas A&M Pressuremeter Probe when seated in a borehole larger than the diameter of the probe considering modulus of pressurized probe much greater than in-situ soil or when inflated in air.

FIG. 1B: Calculated inflation curves for a Self-Boring Pressuremeter Probe when seated in a borehole equal to the diameter of the probe considering modulus of pressurized probe much greater than in-situ soil or when inflated in air.

DETAILED DESCRIPTION OF INVENTION

Figure 2:
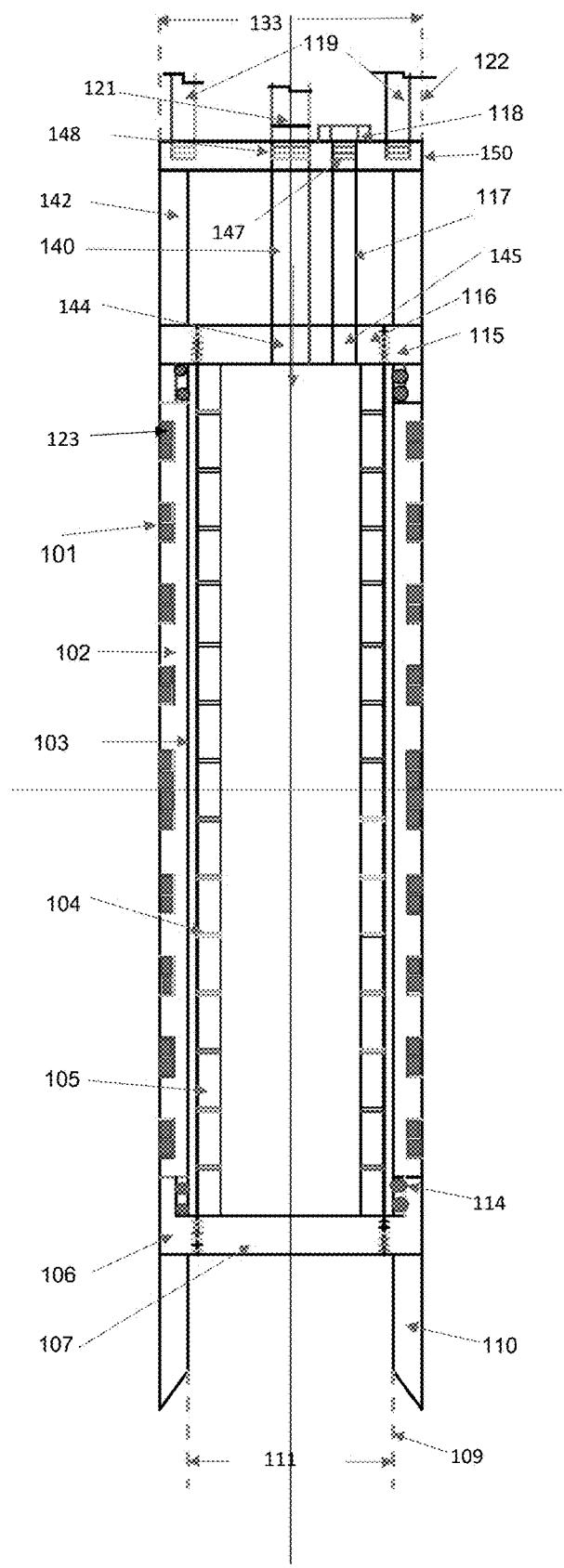
FIG. 2: Schematic detail of a Pressuremeter Probe with an Expandable Jacket, seated in a test hole, when pre-bored test hole drilled hole equal to diameter of this probe where top of the probe to be seated and then pr-bored to a diameter less than that the probe to a depth below where bottom of the probe to be seated, finally then the probe is seated in place by pushing the probe to cut the in-situ soil.

In this application, the expandable jacket on one side surrounds and in contact with the pressuremeter probe and on the other side it is in contact with the test borehole in the full length/height of the probe, to apply horizontal pressure and to produce radial displacement in plane strain conditions in the in-situ soil, for determining relationship between lateral horizontal stress and radial displacement (in horizontal-radial directions). The function of the expandable jacket is to maintain uniform radial displacement, that is to maintain cylindrical shape of the pressuremeter probe throughout its height during a test. The expandable jacket comprises circular-arch shaped segmented plates surrounding the pressuremeter probe. The circular-shaped segmented plates are themselves then surrounded by a plurality of expandable bands or rings. The thickness of the circular-shaped plates with the flexible lateral support provided by expandable bands or rings is designed to maintain its verticality when the lateral forces are applied to it to produce horizontal displacement in radial directions. When the expandable jacket expands, the gap between two adjoining circular arch shaped segmented plates shall increase, it is expected that the in-situ soil shall arch over the gap because these segmented plates are quite thick and shall not infiltrate into the gap and puncture the membrane. However, during testing for commercial purposes, experience shows that infiltration of insitu soil in the gap is the reason for puncture of the membrane, then optional measures to bond the circular arch shaped segmented plates to a thin rubber membrane shall be done to provide extra protection of the membrane covering the porous tube. In this way, both the increase of horizontal stresses and the corresponding increase of radial displacement produced in the in-situ soil shall remain equal throughout the height of the pressuremeter probe.

The pressuremeter probe with the expandable jacket as described in this application, have different methods, i.e., (i) pre-bore either to diameter equal to the diameter of the probe (first method of drilling a test hole), or (ii) pre-bore to a diameter less than the diameter of the probe (second method of drilling) or (ii) self-bore to diameter to less than the diameter of the probe (Third method of drilling). Each of these boring or drilling methods as described above affects the quality of the hole in the in-situ soil or on the degree of undisturbed condition of the in-situ soil or jointed rocks or soft rocks. In medium to hard intact rocks, there is not much difference in boring or coring method as far disturbance of rocks surrounding the bored/cored hole or pocket is concerned, if sufficient precautions have been taken by the driller.

To prepare a good quality of the test hole, the drill bit shall be a three-wing bit for clays, silts and fine sands and a roller bit for gravelly sands, unless otherwise specified in plans and drawings of a project. The bit must allow the drilling mud or slurry to discharge axially against the bottom of the test hole/borehole. Any side discharge will lead to a poor-quality hole, especially in erodible soils. The diameter of the rods must be large enough compared to the diameter of the bit so as to allow good flow of the cuttings up the hole (for example say AW Rods for a 3-in bit).

It is preferable to drill a test hole/borehole generally about 2-3 feet (0.6-0.9 m) below the test depth where the bottom of the pressuremeter probe is to be located to perform the test. The pressuremeter probe can be inflated in a series of equal pressure increments or series of equal volume increments and the test performed in accordance with the procedure described in report No. FHWA-IP-89-008 (Briaud, 1989) or as described in ASTM-D4719. For each pressure increment, a reading of injected volume is taken after 30 and 60 seconds. For each volume increment, a pressure reading is taken at the end of the 15 second increment. (Briaud, 1989). Since the expandable jacket shall make the inflation of membrane more controlled and stable, it may be possible to increase time from 15 or 30 or 60 seconds to more than a minute or so for reading pressure or volume increment to provide more accurate readings for each increment, when pressuremeter tests with expandable jacket are being conducted.

All pressuremeter probes described in this application are surrounded by the expandable jacket whether for soils and intermediate geomaterials or for rock, therefore diameter of the pressuremeter probes becomes outside diameter of the expandable jacket. The pressuremeter probe for soils and intermediate geomaterials consists of a porous tube which is surrounded by the membrane (that is expandable and impervious), which in turn is surrounded by the expandable jacket as described above. The expandable jacket comprises the circular-arch shaped segmented plates which are surrounded by rings or bands, which are expandable. The circular-arch shaped segmented plates are provided with circular grooves in which bands or rings are installed in order to maintain the outside surface of the bands or rings, flush with the outside surface of the segmented circular shaped plates. The thickness of the circular-arch shaped segmented plates is designed to maintain their verticality during the test with lateral support of the bands or rings during the test. When the membrane is inflated, the lateral displacement occurs in bands or rings and therefore bands or rings exert lateral stress on the circular-arch shaped segmented plates and helps in maintaining their verticality. The thickness of porous tube and the circular-arch shaped segmented plates is also designed in order to possess sufficient capacity to effectively push the pressuremeter probe in a prebored/predrilled hole of diameter less than that of the probe into the ground or also when the borehole diameter is equal to that of the probe.

In the first method, the hole shall be drilled carefully to a diameter equal to the diameter of the pressuremeter probe to the desired test depth. After which the pressuremeter probe shall be pushed to the test depth by the same drill rig which was used to drill the hole. If necessary, the drill rig may be held by soil anchors to provide adequate down thrust to push the probe downwards to desired depths. The quality of undisturbed soil will not be so good as expected in the second and third method, but the drilling and testing will be quite fast.

In the second method, the hole is pre-drilled/pre-bored to a diameter about equal to the diameter of the pressuremeter probe up to the top of the designated test depth and below which the hole is predrilled/prebored to a diameter less than the diameter of the pressuremeter probe to a depth which is some distance below the designated bottom of the probe. After which the pressuremeter probe is first lowered down up to the top of the hole and then with the downward force of the drill rig, or CPT rig or any other type moveable loaded box or unmovable box/platform, the pressuremeter probe is pushed slowly till its top is seated at the top of the designated test depth. Slow speed to push down is important in order for the cut soil to fall in the borehole below the bottom of the pressuremeter probe any time during pushing it. In this way, the cut soil will not push into in-situ soil and will not disturb the in-situ condition of the in-situ soil and therefore, in-situ soil shall remain undisturbed. The diameter of the bored hole (111) below the probe generally shall be about equal to the inside diameter (111) of the cutter ring (110) attached at the end of the probe.

The third method of drilling/installation involves using the self-boring pressuremeter probe (SBPMT) for soils and intermediate geomaterials. First the borehole equal to the diameter of the self-boring pressuremeter probe is bored/drilled, up to the depth where top of the probe will be eventually seated for the first test, that is when the pressuremeter probe has been pushed to seat the bottom of the pressuremeter at the bottom of the test depth. Then the hole will be bored by a self-boring pressuremeter probe (SBPMT) to a diameter less than the diameter of the self-boring pressuremeter probe to some distance below the depth where the bottom of the self-boring pressuremeter probe will be seated. Then the self-boring pressuremeter probe shall be pushed down slowly under vertical force of the drill rig, or CPT rig or a moveable loaded box till the bottom of the probe sits at the bottom of the test depth. After performing the test at a particular test depth, the self-boring pressuremeter probe shall be bored further to a diameter less than the diameter of the probe, and then the pressuremeter probe shall be pushed to the next depth to perform another test, unless some unforeseen circumstances occur. The main difference in the first and second method of installation is that by using the self-boring pressuremeter probe, the testing can be continued to the next test depth without pulling it out of the ground each time after one test, unlike what is to be done in the first method. Both these types of pressuremeter probes shall provide the equal or better quality of the hole in terms of no disturbance to the in-situ soil surrounding the hole. Specialized personnel and a specialized method of self-boring shall not be required, and the local drillers with some supervision by a technician shall be sufficient to perform the test.

The test hole shall be generally stabilized by drilling mud/slurry based on the decision or discretion of the geotechnical engineer of the project. Where the subsurface soils consist of partially saturated or nearly dry sandy soils and clayey silty soils, it may be possible that the test hole may not need to be stabilized by drilling mud/slurry and the test hole may remain stable both during insertion of the probe and during performing the pressuremeter test. The slurry may consist of mineral slurry or bentonite slurry or special chemical slurry. Drilling mud/slurry generally flakes on the inside surface of the test hole. During pushing the pressuremeter probe in a test hole, which is less than the diameter of the probe, the inside surface of the test hole consisting flake cakes of drilling/slurry shall get cut and be removed from the surface of the test hole, maintaining an undisturbed condition of the in-situ soil. However, when the pressuremeter probe is pushed in a test hole which is diameter equal to that of the probe, there is some possibility that some of the flake cakes of drilling mud/slurry may be left in the test hole in the test depth. The boring of a test hole less than that of the pressuremeter shall also help in undisturbed condition of the in-situ soil and shall help in maintaining the in-situ horizontal stresses at rest, before the borehole is further scrapped/cut to a diameter equal to the diameter of the pressuremeter probe by the cutting ring located at the end of the pressuremeter probe.

(a) Expandable Jacket Surrounding Pressuremeter Probe for Performing Tests in Soils and Intermediate Geomaterials Using Pre-Boring Method FIG. 2 shows the schematic detail of a pressuremeter probe with the expandable jacket surrounding it. For this probe a bore hole equal to its diameter is drilled to a depth where or when the probe's top will be located at the top of the test depth. Thereafter, the bore hole of diameter (111) less than the diameter of the probe is drilled to a depth some distance below where the bottom of the probe is to be seated. The pressuremeter probe consists of a porous tube (105) surrounded by and in contact with a membrane (103) which is expandable and impervious. The membrane (103) is sealed to the porous tube (105) at its top and bottom ends by an O-ring (114) or more than one O-ring (114) so that the system becomes water tight or leak proof to maintain high pressures during the test. The O-rings (114) are expandable and impervious. The O-ring or O-rings (as the case may be), at the top end is/are held firm by a circular ring (115), which is thread connected to the top plate (116). The O-ring or O-rings (as the case may be), at the bottom end is/are held firm by a circular ring (106), which is thread connected to the bottom plate (107). A plurality of circular-arch shaped segmented plates (102) surround and are in contact with the membrane (103). A plurality of circular grooves (101) is made in the circular-arch shaped segmented plates, in which rubber bands or rings (123) are installed to maintain the circular-arch shaped segmented plates to remain vertical and of cylindrical shape and in contact with the membrane (103). The method to seal the membrane for making it leak proof as used by the existing pressuremeters can also be used.

The porous tube (105) has a plurality of straight holes (104) in a grid pattern to let the pressurized fluid to pass through holes (104) to pressurize the membrane to expand, and in turn to let the expandable jacket expand, maintaining a cylindrical shape throughout its height and to apply lateral pressure on in-situ soil to radially displace the in-situ soil uniformly throughout the expandable zone of the in-situ soil. The porous tube at its ends shall be weld or thread connected to top (116) and bottom (106) plates. Weld connection if selected shall be from the inside area of the porous tube (105) at its top and bottom. If the choice is for thread connection, then connection with an O-ring shall be provided to seal the porous tube as leak proof at its top and lower ends. The circular rigid ring (142) of the guard cell at its base shall be suitably thread or weld connected to the circular ring (115) at its bottom end. The circular ring (142) at its top shall be thread connected to rigid circular plate (150) and shall perform as a rigid guard cell to limit the decompression of soil near top of the circular arch shaped segmented plates. Thread connection is also shown in FIG. 5C. A top plate (150) shall be appropriately weld or otherwise thread connected to top of the circular rigid ring (142), in a manner similar to as shown in FIG. 5B, FIG. 5D. The threaded port shall be provided on the top plate (150) to connect the drill rod (119) to lower down and push the pressuremeter probe downwards or pull out the ground after the test. A tube (140) for fluid shall be thread connected with O-rings in between the plate (150) and plate (116) in the threaded holes (148 and 144) to let the fluid flow through to pressurize the membrane during the test. The hole in the top plate (150) shall have threads to connect the pressure fluid hose or pipe (121). The vent pipe (117) shall be similarly provided to connect to the plate (116) and plate (150). A hole in the plate (150) above the vent pipe (117) shall be similarly provided with threads to connect the vent plug (118) to release air while filling the pressure fluid in the porous tube (105) when needed. The cutter ring (110) shall be thread connected with O-ring or weld connected to circular ring (106) in a similar manner as shown in FIG. 5C or FIG. 5D. When a test has been performed, the probe shall be pulled out from the ground with attached drill rods. Next test shall be performed by following the same steps of drilling further and seating the probe as explained in the first few sentences at the top of this section. Above the pressuremeter probe, the diameter of the test hole (133) is equal to that of the pressuremeter probe. Below the cutter ring (110), diameter of drilled hole (111) is equal to the inside diameter of the cutter ring (110), i.e., less than diameter of the pressuremeter probe. The connections between various structural elements such as plates and circular rings as shown in figures or in description may be redesigned again during assembly, machining and manufacturing the probe and the final drawings prepared for the machine shop for industrial production accordingly.

Figure 3:
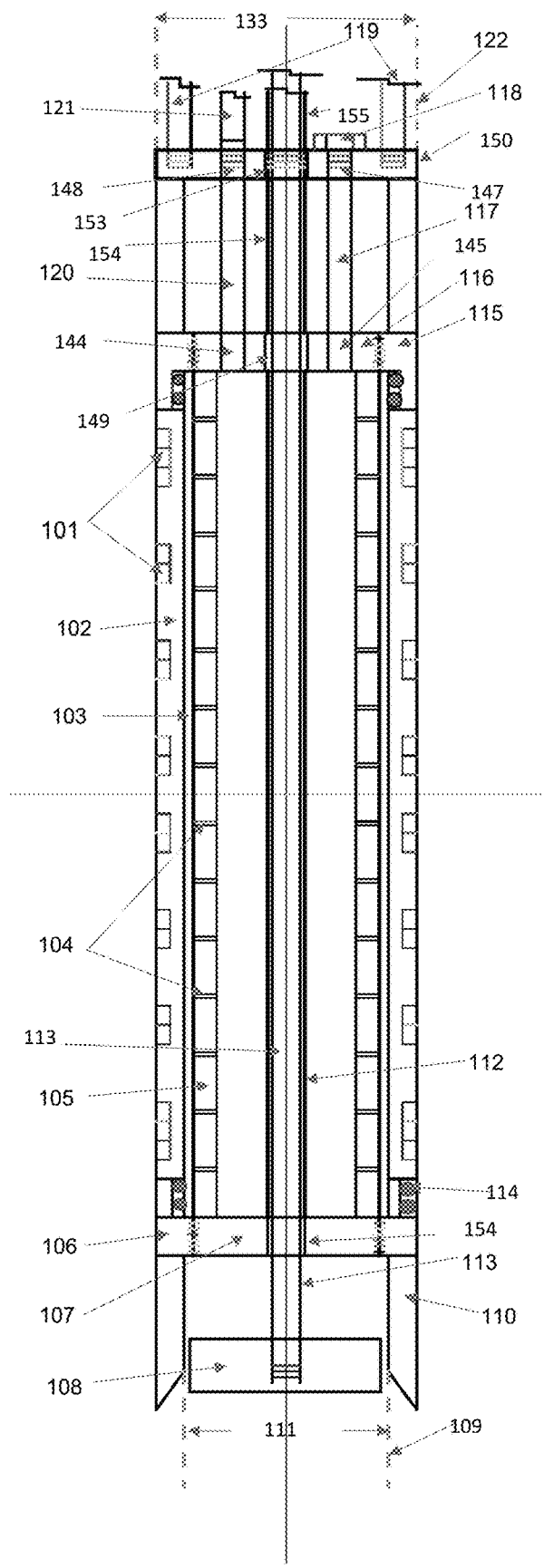
FIG. 3: Schematic detail of a Pressuremeter Probe with an Expandable Jacket, seated in a test hole, when pre-bored test hole drilled hole equal to diameter of this probe where top of the probe to be seated and then self-bored to a diameter less than that the probe to a depth below where bottom of the probe to be seated, finally then the probe is seated in place by pushing the probe to cut the in-situ soil.

(b) Expandable Jacket Surrounding Pressuremeter Probe for Performing Tests in Soils and Intermediate Geomaterials Using a Combination of Pre-Boring and Self-Boring to a Diameter Less than Diameter of the Probe FIG. 3 shows the schematic detail of a pressuremeter probe which is lowered down in a hole using a combination of pre-boring to diameter equal to that of the probe initially and self-boring to a diameter less than diameter of the Probe. The schematic details are somewhat similar as explained in FIG. 2 to perform the pressuremeter test. The layout and details for porous tube, membrane, O-rings, circular-arch shaped segmented plates, bands or rings and cutter rings remain the same as shown in FIG. 2. As shown in FIG. 3, in the center of the probe, two pipes, first pipe (113) which connects to the auger bit, passes through the second pipe (155,154 and 112). After lowering down the inner pipe through the outer pipe (112) to below the pressuremeter probe, the drill/auger bit (108) is attached at the bottom of the first pipe (113). The pipe (155) is screwed into the threaded hole (153) in circular plate (150) and sealed with an O-ring to remain leak proof (Note: O-ring/O-rings for connections has not been shown in FIG. 3). The Second pipe surrounds the first pipe (113) to let the drill cuttings flow through the annular space between first and second pipes back to ground surface. The annular space between the two pipes (112 and 113) should be sufficiently large to let the cuttings made by auger flow out to the ground surface. The pipe (155) need not be etpended to the ground surface as the cuttings will flow out through the drill rods to the ground surface. The Pipe (154) is either weld connected or thread connected with O-ring at its top end in threaded hole (153) to plate (150) at its upper end and weld connected or thread connected with O-ring in threaded hole (149) to plate (116) at its lower end. The pipe (112) is either weld connected or thread connected with O-ring at its top end in threaded hole (149) to plate (116) at its upper end and weld connected or thread connected with O-ring in threaded hole (154) to plate (107) at its lower end.

As shown in FIG. 5B, cutter ring (110) with its mail screw (160) is screwed in the circular ring (106). As shown in FIG. 5C, the circular guard ring (142) with its mail screw (161) is screwed in the circular ring (115). Another option is to connect 142 and 115 (or 110 to 106) by a circular plate and screws (163) as shown in FIG. 5D. As shown in FIG. 5E, fluid pipe or hose (121) carrying pressurized fluid or gas is thread connected using the fitting (164, 165) in threaded hole 148 to the circular plate (150). The fluid pipe (140 or 120) is either welded or thread connected to at its upper and lower ends with fittings (165,164 as shown in FIG. 5E) to the circular plates (150) and (116), respectively. Vent Plug (118) is a thread connected with an O-ring (166 shown in FIG. 5F) and the vent pipe (117) is either weld connected or thread connected with fittings (164,165) in threaded holes (147 and 145) with fittings (164,165), to circular plates (150 and 116), respectively. All fittings shall be compression fittings or fittings with O-rings.

Figure 4:
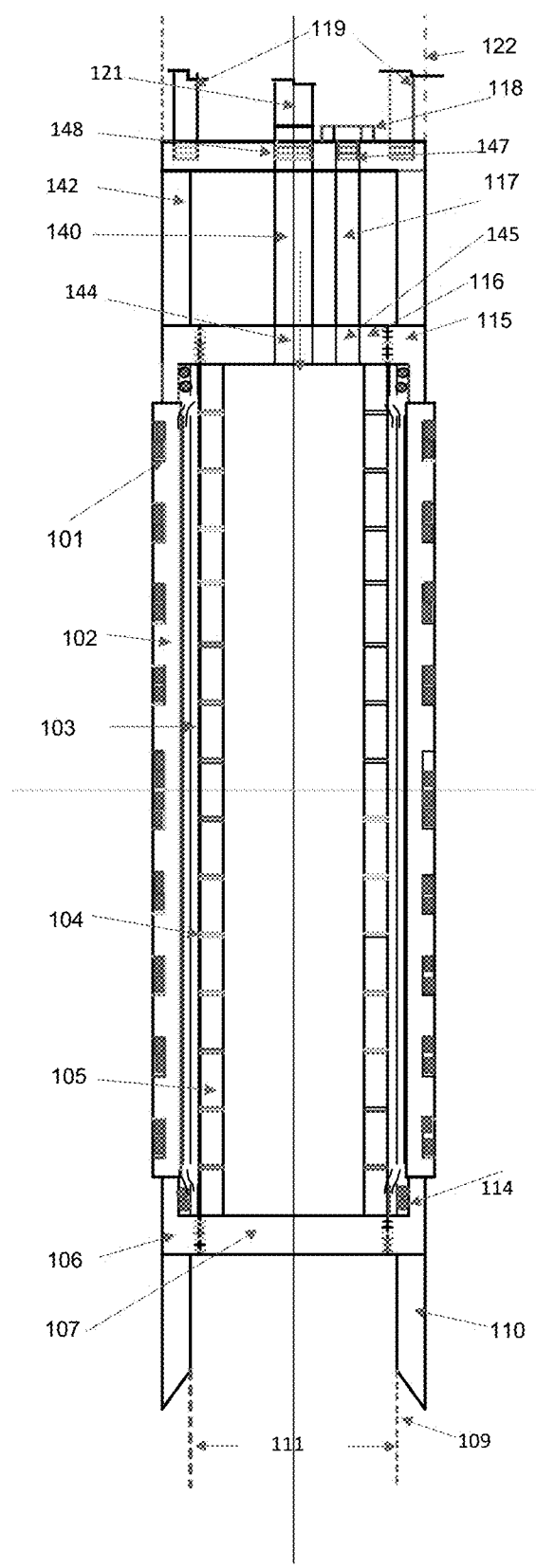
FIG. 4: Schematic detail of a Pressuremeter Probe with an Expandable Jacket when inflated either in air or in a borehole, while maintaining cylindrical shape with uniform radial displacements throughout the height of the probe.

FIG. 4 shows the expansion of the pressuremeter probe with an expandable jacket during the test to determine lateral pressure versus radial displacement/expansion relationship when the probe maintains its cylindrical shape with uniform radial displacement throughout the height of the expanding length of the probe. As can be seen in this figure, the expandable jacket radially expands, maintaining its cylindrical shape and verticality with uniform radial displacement. The guard Cells (142 and 110) limit decompression of the soil near the ends of the expanding zone, because the guard cells are in contact with the in-situ soil.

Figure 5A:
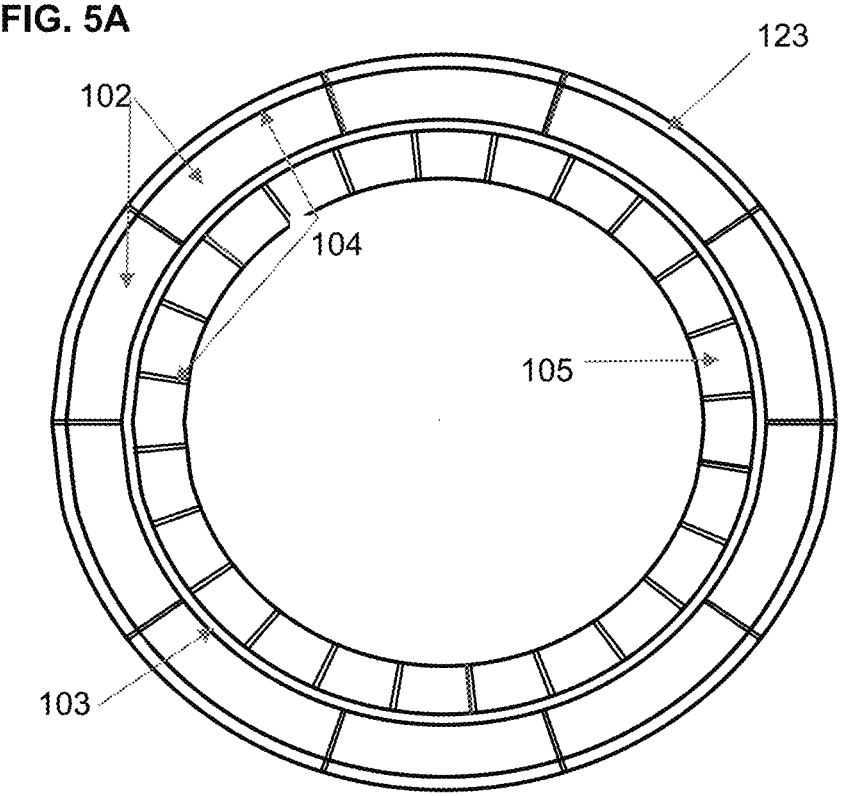
FIG. 5A: Horizontal cross-section at the mid-depth of a Pressuremeter Probe with an Expandable Jacket.
Figure 5B:
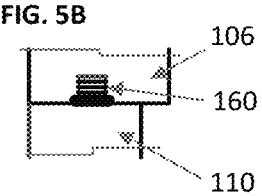
FIG. 5B: Detail showing circular cutter ring (110) with threaded mail screwed in circular ring (106).
Figure 5C:
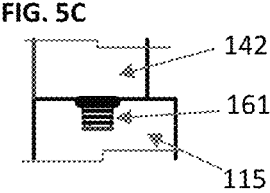
FIG. 5C: Detail showing circular guard ring (142) with threaded mail screwed in circular ring (115).
Figure 5D:
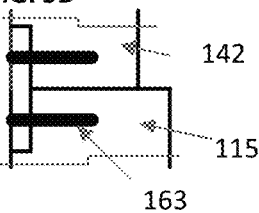
FIG. 5D: Another option for connecting circular guard ring (142) to circular ring (115) by a circular plate using headless screws or countersunk screws.
Figure 5E:
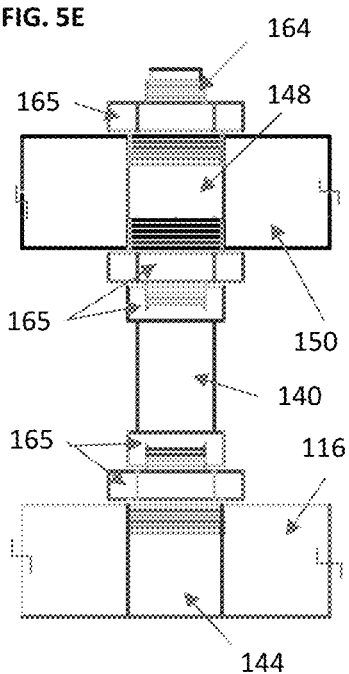
FIG. 5E: Detail showing fluid pipe (140) connection to circular plate (150) and to circular plate (116) using compression fittings or fittings with O-rings.
Figure 5F:
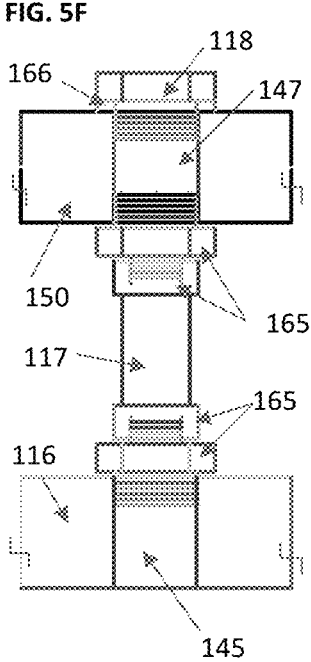
FIG. 5F: Detail showing vent pipe (117) attachment to circular plate (150) and circular plate (116) and attachment of vent plug using compression fittings or fittings with O-Ring.

FIG. 5A shows the schematic plan view at the mid-height of the probe. The number of holes in the porous tube shall depend upon the diameter of the probe and borehole. The number of circular-arch shaped segmented plates shall also depend on the diameter of the probe and borehole. Expandable property of an expandable jacket to perform requires at least two circular arch shaped plates. With increase in diameter, the number of circular-arch shaped segmented plates shall increase from a minimum of two for example to four, six, eight, 10, 12 etc., and even more than twenty depending on the size of the borehole and the probe.

Figure 9A:
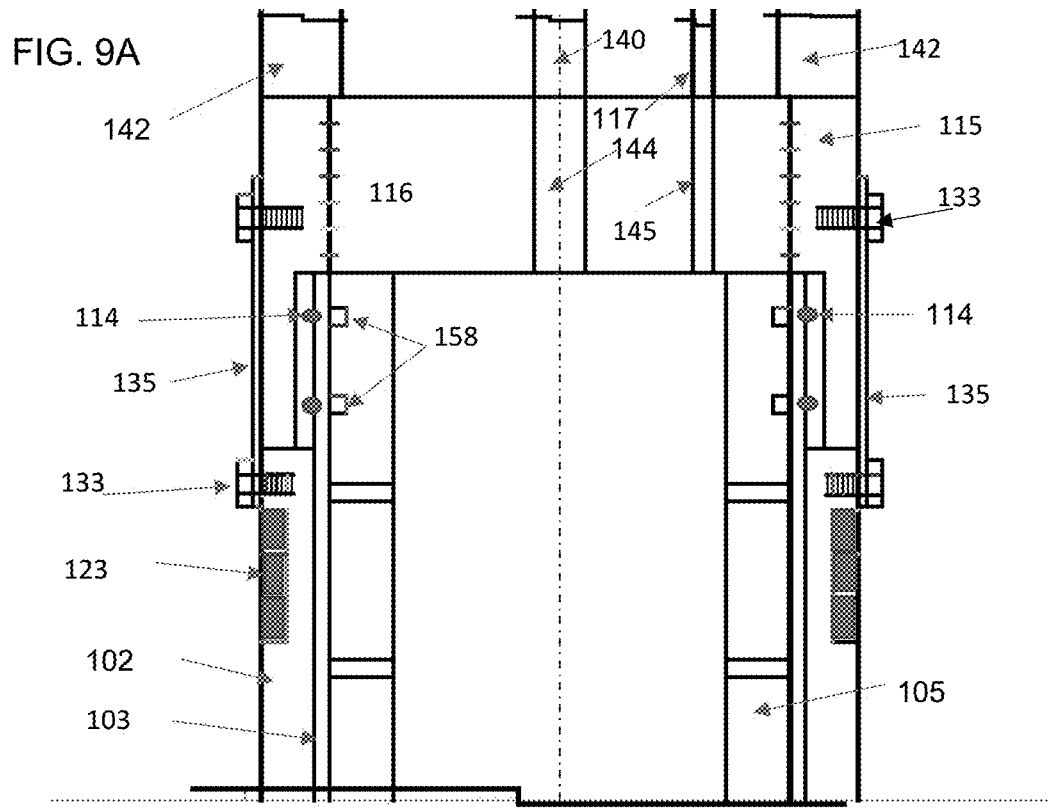
FIG. 9A: Schematic detail showing removable attachments to initially assemble the circular shaped segmented plates around membrane and porous tube of pressuremeter probes for performing a pressuremeter test in soils and intermediate geomaterials.

IN FIG. 9A, removable attachments to accurately assemble the circular-arch shaped segmented plates around the membrane have been shown. Removable plates (135) are fastened to each circular-arch shaped segmented plate (102) at the bottom by lower removable screws (133) and to the circular ring (115) by upper removable screws (133) at the top. After installing the bands/rings in the circular grooves (101) around the circular-arch shaped segmented plate (102), the removable attachments (removable circular plate and removable screws) are removed. There are other methods available to assemble the circular-arch shaped segmented plates, as described by Gupta (2016, 2017 and 2018). When the diameter of the probe is very small, these circular-arch shaped segmented plates (102) can be assembled by one person holding the circular-arch shaped segmented plates around the probe and another person installing the bands or rings. But all these methods shall not be as accurate as the one shown in FIG. 9A, FIG. 10A. 10B.

Figure 10A:
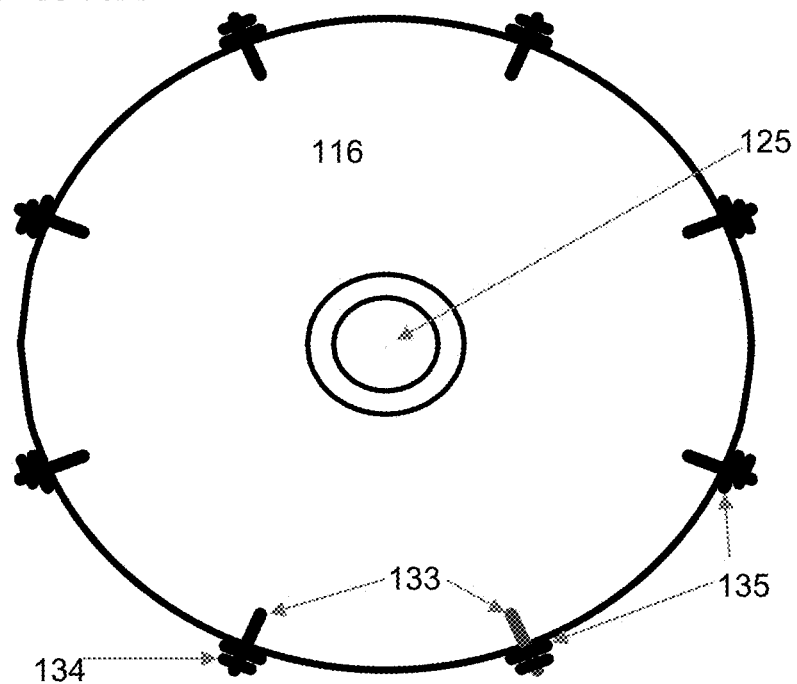
FIG. 10A: cross-section detail for installation of circular arch shaped segmented plates at the level of top removable attachment for a pressuremeter probe to perform tests in soils and geomaterials.
Figure 10B:
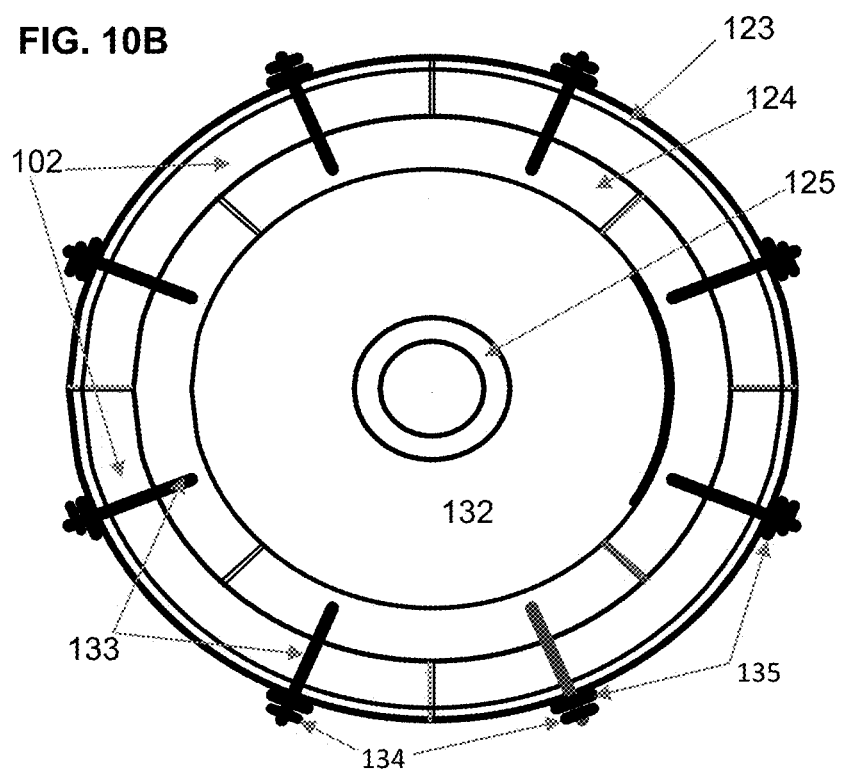
FIG. 10B: cross-section detail for installation of circular arch shaped segmented plates at the level of top removable attachment for a pressuremeter probe to perform tests in soils and intermediate geomaterials.

In FIG. 10A, the layout plan at the level of upper screws fastening the circular plate (135) to the circular ring (115) have been shown. In FIG. 10B, the layout plan at the level of lower screw fastening the circular plate (135) to each and every circular-arch shaped segmented plate at their mid-points have been shown. The optional rectangular or circular grooves (158) as shown in FIG. 9A are provided just behind the O-rings so that O-rings push the membrane in those grooves to make a leak proof/water proof joint.

The locations of the circular grooves for bands or rings and their total number in the circular-arch shaped segmented plates shall be suitably designed so that the bands or rings together with designed thickness of the circular-arch shaped plates shall maintain verticality of the circular-arch shaped segmented plates without forming barrel shape for various sizes/diameter and heights of the probe and borehole. The expandable bands and rings both can have either rectangular or square or circular cross-section or any other shape manufactured in the industry. The thickness/diameter, modulus of elasticity and the tensile strength of expandable rings/bands and their total number shall be selected based on the required lateral resistance to be exerted by the expandable jacket on the cylindrical soil specimen during the test. Bands and rings are manufactured in various thicknesses and widths, diameters, tensile strength and modulus of elasticity. The thickness of the expandable and impervious membrane shall be designed based on diameter of the probe, maximum radial displacement and the magnitude of the fluid and gas pressures applied to expand the probe, in order to resist the applied pressures without leak and bursting. The maximum possibility of bursting of expandable and impervious membrane may be at the top and bottom ends of the circular-arch shaped segmented plates, therefore, after experience as obtained from a several tests, an extra layer of membrane beginning from its end to some distance below top end and above bottom end of circular-arch shaped segmented plated may be provided as an option. The extra layer of the membrane shall be seated in a circular groove cut in the porous tube, such that the extra layer of membrane is flush with the outside surface of the porous tube. The connections between various structural elements such as plates and circular rings as shown in figures or in description may be redesigned again during assembly, machining and manufacturing the probe and the final drawings prepared for the machine shop for industrial production accordingly.

Figure 6:
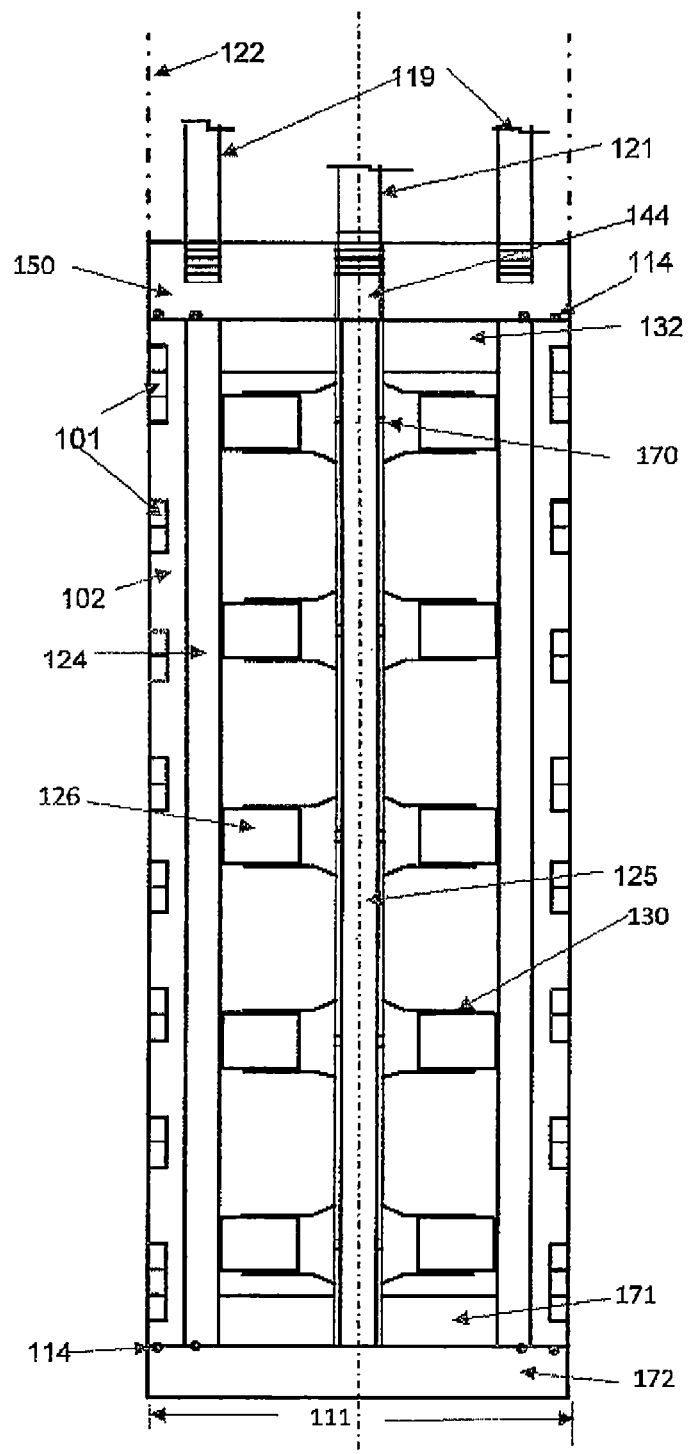
FIG. 6: Schematic detail of a Pressuremeter Probe with two layers of circular arch shaped plates staggered over each other for performing a pressuremeter test in rock.
Figure 8A:
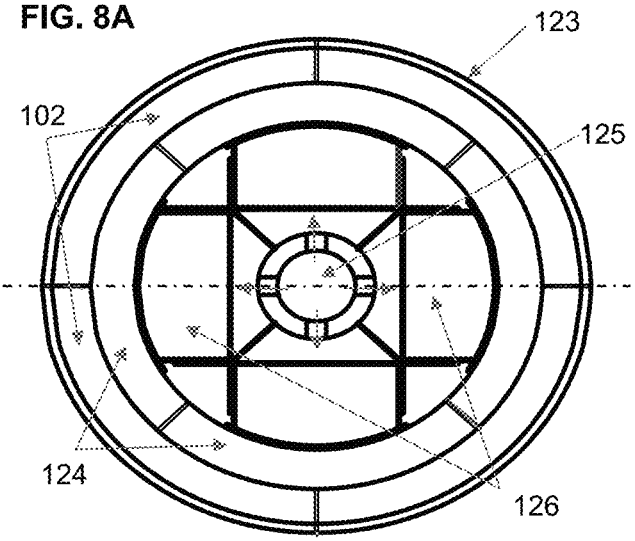
FIG. 8A: Cross-sectional detail at mid-height of a pressuremeter probe with four piston assembly and two layers of four circular arch shaped segmented plates staggered over each other at each selected depth.
Figure 11A:
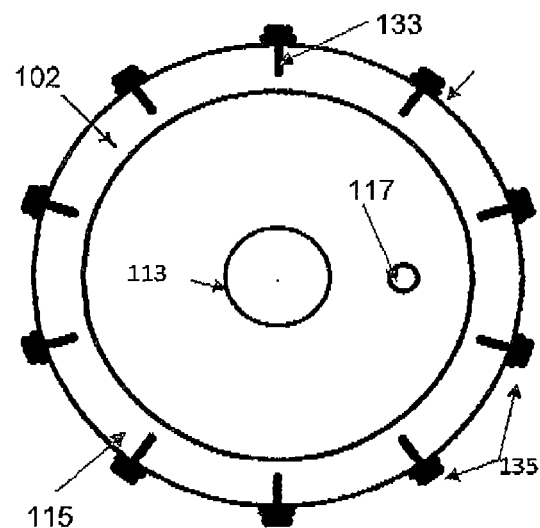
FIG. 11A: cross-section detail for installation of circular arch shaped segmented plates at the level of top removable attachment for a pressuremeter probe to perform tests in rock.

(c) Expandable Jacket Surrounding Pressuremeter Probe for Performing Tests in Rocks Using Hydraulic Jacks The schematic details of a pressuremeter probe for performing pressure meter testing in rocks is shown in FIG. 6. This probe comprises a plurality of hydraulic jacks (130) at selected vertical spacing along the height of the probe, to apply pressure in horizontal and radial directions on the loading circular arch shaped segmented plates (124). The loading circular arch shaped segmented plates (124) surround and are in contact with the hydraulic jacks (130). Second layer of circular arch shaped segmented plates (102) surrounds and is in contact with the loading circular arch shaped segmented plates (102) and staggered over each other such that clear joint between the second layer of loading circular arch shaped segmented plates (124) coincides with mid-point of the loading circular arch shaped segmented plates (124), as shown in FIG. 8A. The outside surface of the second layer of the circular arch shaped segmented plates (102) may also greased for them to slide smoothly in contact with rock. The contact surface between the two layers of the circular arch shaped segmented plates is greased frequently in order for one layer to slide on the other during expansion of the expandable jacket. The second layer of the circular arch shaped segmented plates is surrounded and in contact with a plurality of bands or rings (123) (not shown in FIG. 6), which are installed in a plurality of circular grooves (101) as shown in FIG. 6, FIG. 8A and FIG. 11A. To limit or stop water or fine rock fragments or soil to enter, O-rings (114) has been provided in circular or rectangular grooves such that the O-rings are in contact with ends of the circular arch shaped segmented plates both at their top and bottom.

The locations of the circular grooves for bands or rings and their total number in the circular-arch shaped segmented plates shall be suitably designed so that the bands or rings together with designed thickness of the circular-arch shaped plates shall maintain verticality of the circular-arch shaped segmented plates without forming barrel shape for various sizes/diameter and heights of the probe and borehole. The expandable bands and rings both can have either rectangular or square or circular cross-section or any other shape manufactured in the industry. The thickness/diameter, modulus of elasticity and the tensile strength of expandable rings/bands and their total number shall be selected based on the required lateral resistance to be exerted by the expandable jacket on the cylindrical soil specimen during the test. Bands and rings are manufactured in various thicknesses and widths, diameters, tensile strength and modulus of elasticity.

Figure 11B:
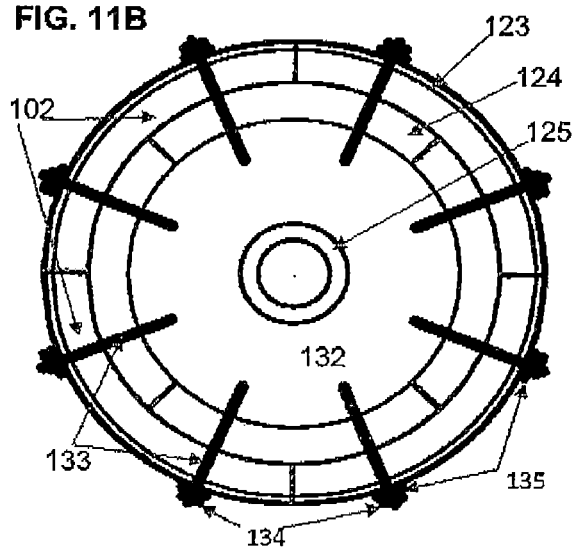
FIG. 11B: cross-section detail for installation of circular arch shaped segmented plates at the level of lower removable attachment for a pressuremeter probe to perform tests in rock.
Figure 11C:
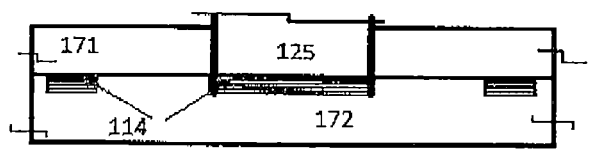
FIG. 11C: Attachments of bottom plate to circular ring and fluid pipe to bottom plate.

A test hole shall be pre-drilled in the rock. Drill rods (119) to push the probe downwards in the test hole or to pull the probe out of the ground shall be screwed in the top circular plate (150). The fluid hose or pipe (121) shall be thread connected with O-rings with fittings in the threaded hole (140) in circular plate (150). A tube (125) shall be weld connected or thread connected with O-Ring to the circular plates (150, 172). The tube (125) shall have holes (170) to let fluid flow into the hydraulic piston cylinder (130). The piston cylinder (126) which is in contact with loading circular arch shaped segmented plates (124), when moves shall expand the expandable jacket. The tube (125) is weld connected or thread connected at its top end with circular plate (150) and at its bottom end with the circular plate (172). The circular arch shaped segmented plates (124) initially rest against the circular plate (150) at the top and circular plate (172) at the bottom, but when the piston moves to apply load on the loading circular arch shaped segmented plates (124), these plates also radially and horizontally move. The Circular plates (132 and 171) are welded or thread connected to circular plate (150) at the top and to circular plate (172) at the bottom. These connections have not been shown in FIG. 6. In FIG. 11C, the thread connection with O-ring has been shown for the fluid pipe (125) at its bottom and for circular ring (171). Similar attachments can be made for the fluid pipe (125) at its top and circular ring (132). At the time of making shop drawing for production, the design of attachments may be revised from time to time as experience gained in repeated in-situ testing.

Figure 8B:
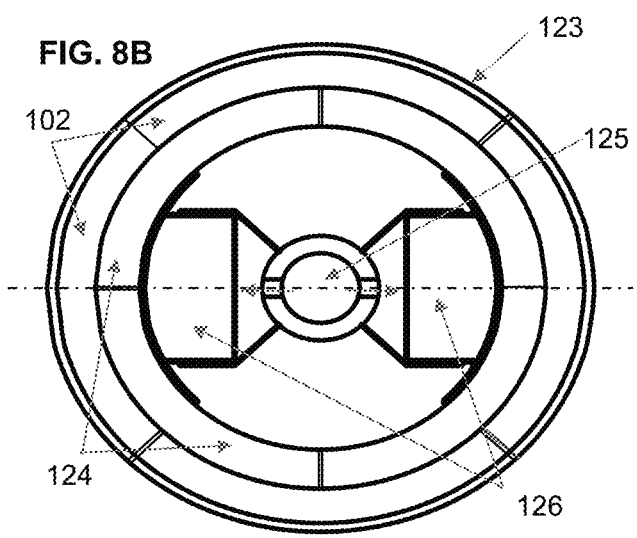
FIG. 8B: Cross-sectional detail at mid-height of a pressuremeter probe with two layers of four circular arch shaped segmented plates staggered over each other and two piston-assembly at each selected depth.
Figure 8C:
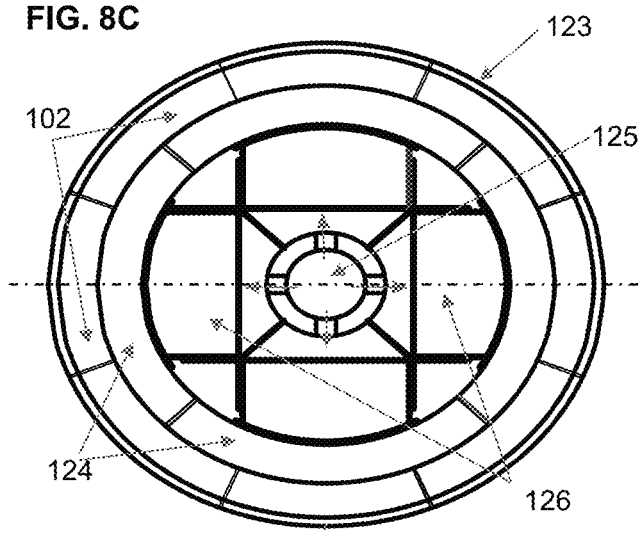
FIG. 8C: Cross-sectional detail at mid-height of a pressuremeter probe with one layer of four loading circular arch shaped segmented plates staggered under another layer of eight of circular arch shaped segmented plates and four piston assembly at each selected depth.

FIG. 8A show plan views when the numbers of jacks are four spaced at 90 degrees along the circumference of the loading circular arch shaped segmented plates (124). In this case the number of expanding circular arch shaped segmented plates (102) and loading circular arch shaped segmented plates (124) are four, and are staggered on each other. FIG. 8B show plan views when the numbers of jacks are two spaced at 180 degrees along the circumference of the loading circular arch shaped segmented plates (124). In this case the number of expanding circular arch shaped segmented plates (102) and of the loading circular arch shaped segmented plates (124) are staggered in a different way. FIG. 8C shows another staggering plan view, where number of hydraulic jacks and loading circular arch shaped segmented plates (124) are four, but by staggering in an appropriate way, the number of expanding circular arch shaped segmented plates (102) to share the load are eight for the same size of test hole. Properly staggering the second layer on the first layer, on each loading circular shaped arch shaped segmented plates, three circular arch shaped segmented plates of the second can be staggered, making a total of 12 circular arch shaped segmented plates of second layer on four loading circular arch shaped of the first layer. For very small holes only two hydraulic jacks are sufficient. When diameter of holes is bigger than number of jacks can be three spaced at 120 degrees, or four spaced at 90 degrees or six spaced at 60 degrees or even nine spaced at spaced at 40 degrees apart along the circumference of the test hole. The staggering pattern for two layers of the circular arch shaped segmented plates (124 and 102) shall be appropriately designed to equally distribute load on the test hole walls.

Figure 7:
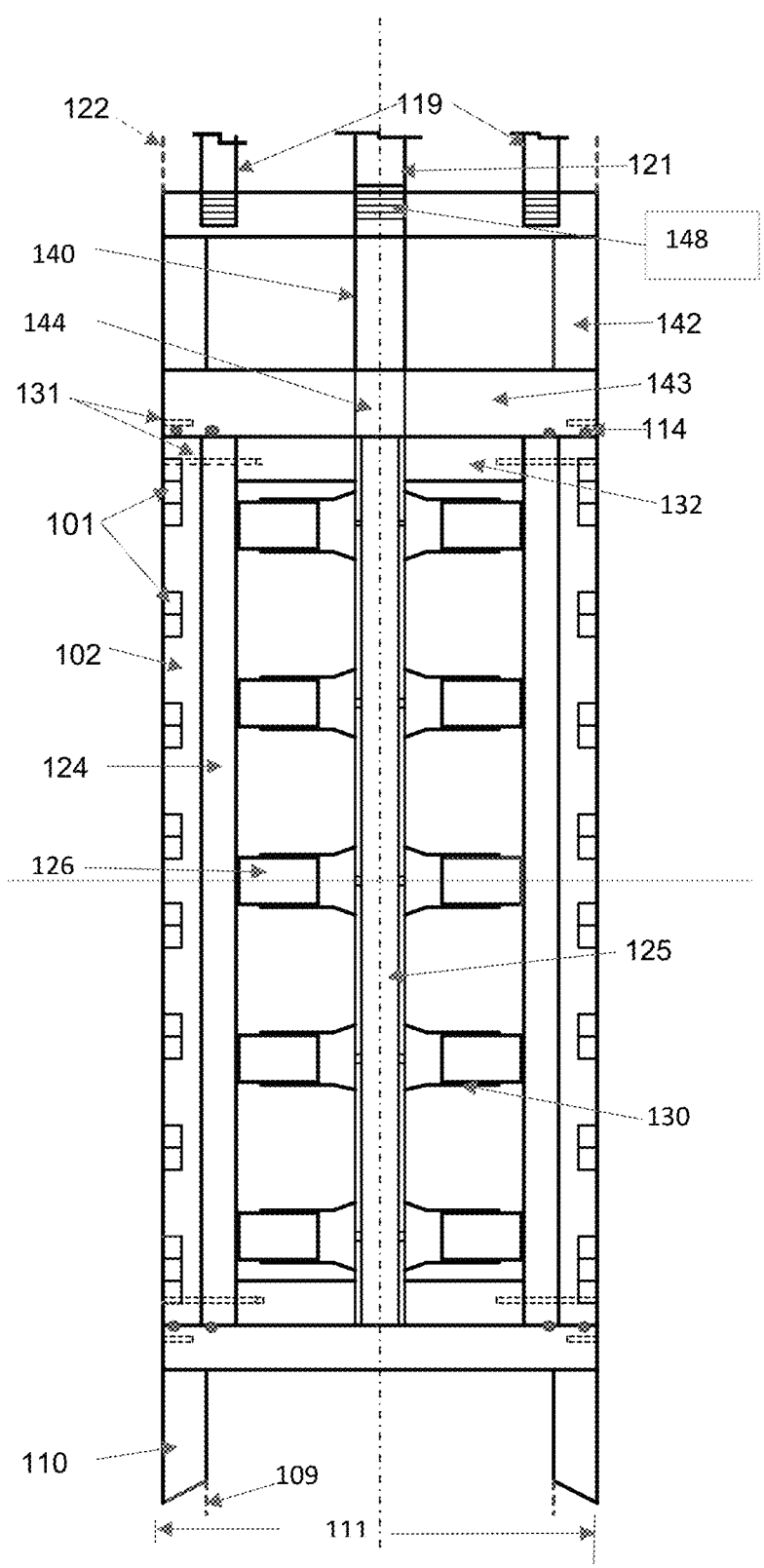
FIG. 7: Schematic detail of a Pressuremeter Probe with two layers of circular arch shaped plates staggered over each other for performing a pressuremeter test in soils and intermediate geomaterials.

The application of piston rings in a hydraulic system is highly diverse. For the pressure build-up in a hydraulic pump and cylinder, the piston rings are crucial for the system to operate. Often the requested sizes are no longer available in stock, therefore the manufacturer manufactures the piston rings along with hydraulic pump and cylinder. A piston seal/piston ring works by containing pressure on one side of a piston without leakage. This allows maximum mechanical effort to be applied to moving the piston along the bore of a cylinder. Piston seals are intended to prevent leakage past the piston and therefore maximize the efficiency of the system. Today mostly Buna-N and urethane for rings/seals are materials of choice. Piston rings come as three rings. They are the top compression ring, then the intermediate compression ring and finally the oil control ring. Rings with a groove in the outside diameter and a 'pip' mark or dot on the side must be installed with the groove toward the bottom of the piston. It is a good idea after installation, all rings on the pistons to be rechecked for each ring for correct installation. Each manufacturer of hydraulic pump and cylinder have their own proprietary details about hydraulic systems of various sizes and hydraulic capacity in terms of the maximum hydraulic pressure. No detail about the rings regarding their layout etc., has been shown in FIG. 6 and FIG. 7. The manufacturer who will manufacture the hydraulic system as shown in FIG. 6 and FIG. 7 will draw up plans for piston rings, which is customary in the industry. Like Goodman Jack, bearing plate pressure up to about 9300 psi (64.12 MPa) or more for hard rocks and up to about 5544 psi (38.22 MPa) or more are to be designed for pressuremeter probes as shown in FIG. 6. IN HPD probes, pressure up to about 2900 psi (20 MPa) is applied.

Figure 9B:
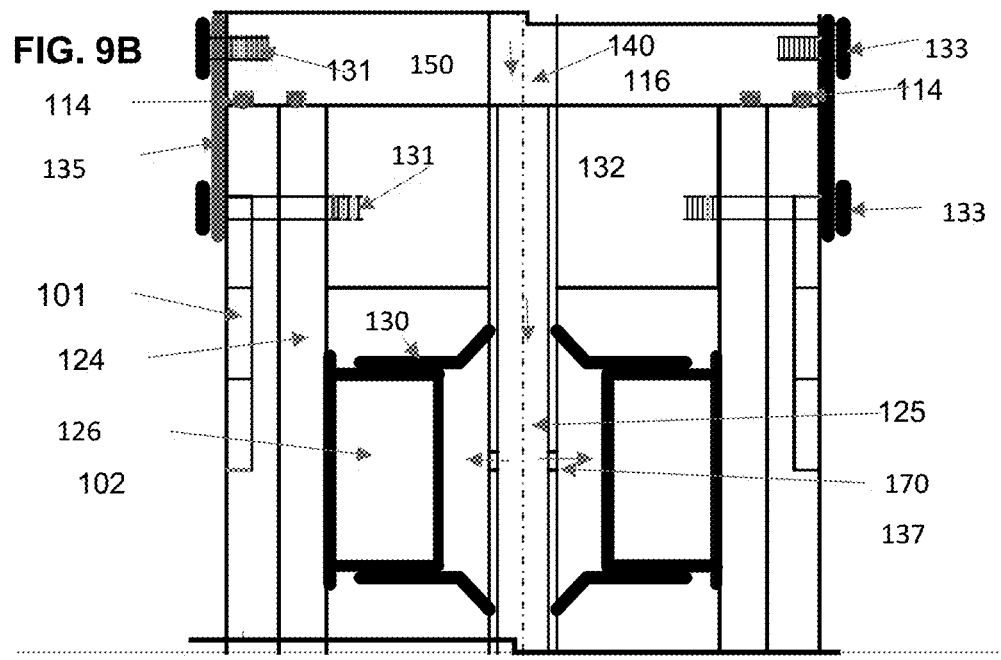
FIG. 9B: Schematic detail showing removable attachments to assemble two layers of circular shaped segmented plates around piston assembly of pressuremeter probes for performing a pressuremeter test in rock.

In FIG. 9B shows a scheme to assemble the two layers of the circular arch shaped segmented plates (124 and 102) using removable attachments. The removable plates (135) are fastened to the top circular plate (150) by removable screws (133) at the top and also to two layers at each circular arch shaped segmented plates (124 and 102) by removable screws (133) to the circular ring (132). Similarly, the removable plates (135) are to be fastened to the bottom circular plate (172) by removable screws (133) and the two layers of each circular arch shaped segmented plates (124 and 102) by removable screws (133) to the circular ring (171). The plan view at the level of upper threaded holes (131) is shown in FIG. 11A. The removable plates (135) are fastened to the circular ring (150) vertically above the location of the mid-point of each and every circular arch shaped segmented plate. The plan view at the level of the lower removable screw is shown in FIG. 11B. In this view, the same removable plates (135) are fastened to the to both layers of each circular arch shaped segmented plates (124 and 102) at their mid-points by screws (133). After which, bands or rings (123) are installed in the circular grooves (101), and then all removable screws (133) and removable plates (135) are removed. This is one way to accurately assemble the two layers of the circular arch shaped segmented plates (102 and 124). There are other schemes (Gupta, 2018), which may not so accurate to assemble in this case.

(d) Expandable Jacket Surrounding Pressuremeter Probe Using Hydraulic Jacks for Performing Tests in Soils, Intermediate Geomaterials The schematic detail of the pressuremeter meter using hydraulic jacks for performing pressuremeter tests in soils, and intermediate geomaterials is shown in FIG. 7. This type of pressuremeter probe can also be used for performing tests in weak rocks (for example shale) or jointed rocks. The only difference in schematic detail as shown in FIG. 6 and FIG.

7 is that a circular guard tube (142) and cutter ring (110) have been attached at the top and bottom circular plates (150 and 172) to limit decompression at the ends of the expandable jacket during the test. The cover plate (143) is attached to the circular guard (142). The drill rod (119) is attached to the cover plate (143). The fluid pipe in between circular plate (150) and cover plate (143) is attached. The fluid hose/pipe (121) from the control panel at the ground surface is fastened to the cover plate (143). All other details remain the same. Because, during testing in soils and intermediate geomaterials, not so high lateral pressures are required, therefore the hydraulic capacity of jacks will be reduced and designed to apply bearing plate pressure generally in the range of about 10 to 20 MPa (1500 to 2900 psi).

(e) Measuring System for Above Described Four Pressuremeter Probes Surrounded by Expandable Jacket The existing systems being used in various types pressuremeters for testing can also be used to measure or calculate radial displacement and applied pressures in the pressuremeters with expandable jacket. Menard Pressuremeter Probe consists of a read-out unit, which consists of a control panel, equipped with devices to regulate the pressure applied to the probe and read its volume changes with pressure increments and time. A nitrogen cylinder provides the pressure source. The box stands on a tripod. It includes the 800 cubic centimeter volumeter with a sight tube, a main pressuremeter regulator, a differential pressure regulator, pressure gauges 0-2.5 and 0-60 bar for measuring pressure in probe and guard cells. A coaxial or twin tubing, flexible, high resistance with small dilation, connects the probe to the control unit. The same system with appropriate changes can be used for the pressuremeter probes with expandable jackets for performing pressuremeter tests in soils and intermediate geomaterials, as described in this application. Texas pressuremeter uses a mechanical actuator which displaces a cylinder piston that travels within a cylinder filled with inflation fluid. It is supported on four columns and has two crank handles, a volume counter, a high precision digital gauge, and a readout box for pressure and volume reading. Similar or the same system can be appropriately adopted with the pressuremeter probes with expandable jacket for measuring volume and pressure increments.

In SBPMT, the expansion is monitored by three or six strain arms, positioned at 120-degree intervals or six strains spaced 60-degree interval, located at mid-height of the expanding test section. The internal pressure is measured by a strain gaged cell within the instrument. The arms are forced to follow the movements of the membrane by strain gaged leaf springs and hence radial expansion is converted to electrical output. The internal pressure is measured by a strain gaged cell within the instrument. A further two cells are attached to the membrane, 180 degrees apart, and these cells measure the changes in pore pressures. The same system can be attempted appropriately by planning to pass leads through the holes in the porous tube.

In Goodman Jack, two linear variable differential transformers (LVDT) displacement transducers are mounted within the jack. The hydraulic pressure exerted by the jacks is measured by pressure gauge. Same type of existing system of LVDT installing in all hydraulic jacks located at the mid-height can also be used for both types of pressuremeters with expandable jacket and hydraulic jacks for testing rocks, soils and intermediate geotechnical materials, as described in this application.

Tests using the pressuremeter probe with expandable jacket shall be generally conducted and analyzed following ASTM Standard for D4719-2020: Standard Test Methods for prebored pressuremeter testing in soils. Cambridge InSitu Self Boring Pressuremeter has few provisions which are different from those in ASTM D4719-2020. Therefore, some changes could be made while conducting tests using the pressuremeter probe with an expandable jacket and analyzing the data. The calibration of pressuremeter probes with expandable jackets shall be performed by pressurizing the probe and measuring or calculating the radial displacement and pressure, to determine the resistance offered by the probe, generally, using the existing calibration device (Gupta, 2018).

REFERENCES

1. Cambridge INSITU Ltd. (2011), "Pressuremeter Testing in Ruritania", www.Cambridge-insitu.com, Cambridge, UK.
2. Gupta, R. C. (2016). "Expandable Jacket and its Calibration Device for Triaxial Tests on Soils", U.S. Pat. No. 9,383,346 B2, United States Patent and Trademark Office, Alexandria, Va. 20133.
3. Gupta, R. C. (2017). "Test Device for Determining Three-Dimensional Consolidation Properties of Soils", U.S. Pat. No. 9,567,722 B2, United States Patent and Trademark Office, Alexandria, Va. 20133.
4. Gupta, R. C. (2018). "Expandable Jacket for triaxial, unconfined and uniaxial compression tests and test device for three-dimensional consolidation and settlement tests", U.S. patent Ser. No. 10/060,898 B2, United States Patent and Trademark Office, Alexandria, Va. 20133.
5. Hustuild, W. A. (1976). "An analysis of the Goodman Jack", The $17^{th}$ U.S. Symposium on Rock Mechanics, Snowbird, Utah.
6. Menard, L. F. A. (1960). "Device for studying the deformation under load of a homogeneous medium", French Patent FR794886A, French Patent Office, France.
7. In Situ Site Investigation. "High Pressure Dilatometer (HPD)", www.insiyusi.com, Susex, UK.
8. RocTest (2014). "Instruction Manual for Self-Boring Pressuremeter, Model: BOREMAC, www.roctest-group-.com, Canada
9. RocTest (2014). "Texas A&M Pressuremeter, Instruction Manual", www.telemac.com, Canada, USA.
10. Slope Indicator Company (2010). "Introduction and Specifications for Goodman Jack", www.slopeindicator-.com, Stone Mountain, Ga. 30087.

The invention claimed is:

1. A method for determining horizontal stress versus radial strain relationship using a Pressuremeter Probe, the method comprising:
   (i) The pressuremeter probe comprising an expandable jacket surrounding and in contact with a membrane, for determining the horizontal stress versus the radial strain relationship for subsurface soils and intermediate geomaterials;
   (ii) the expandable jacket comprising a plurality of circular arch shaped segmented plates, and bands or rings, which are expandable;
   (iii) the membrane which is impervious and flexible surrounding and in the contact with a porous tube;
   (iv) installing the bands or rings in circular grooves cut in an outside surface of the circular arch shaped segmented plates so that the bands or rings are flush with the outside surface of the circular arch shaped segmented plates;

(v) designing thickness of the circular arch shaped segmented plates in order for them to remain vertical with lateral support provided by the bands or rings;
(vi) the porous tube having a plurality of holes which are provided in a grid pattern to let fluid flow to pressurize the membrane;
(vii) designed thickness of the porous tube to remain vertical when the pressure meter probe is pushed in a test hole which is either equal to diameter of the pressuremeter probe or less than the diameter of the pressuremeter probe;
(viii) attaching the porous tube both at its top and bottom ends to top and bottom circular plates using weld connections or thread connections with compression fittings or fittings with O-rings;
(ix) sealing the membrane both at its top and bottom ends using one or more than one O-ring held in place and covered by a circular ring which is thread connected to the top and the bottom circular plates, in order to make it waterproof and leak-proof;
(x) providing an extra layer of a short piece of the membrane from its ends to a small distance below the top end and a small distance above the bottom end of the circular-arch shaped segmented plates, when it is observed during tests that bursting of the membrane is occurring close to the ends of the circular-arch shaped segmented plates;
(xi) providing a guard cell comprising of a circular tube/pipe, thread connected or weld connected to top circular ring attached to the top circular plate;
(xii) providing a cutter ring comprising of the circular tube/pipe, the top end of which thread connected or weld connected to the bottom circular ring attached at the bottom of the porous tube;
(xiii) the bottom end of the cutter ring having a knife edge in order to scrap/cut test hole walls to the size of the pressuremeter probe;
(xiv) the top circular plate attached at the top of the porous tube, having two threaded holes, one for a fluid pipe and other for a vent pipe;
(xv) the guard cell provided with a cover plate;
(xvi) attaching the guard cell to the cover plate by the weld connection or the thread connection;
(xvii) attaching the fluid pipe and the vent pipe in between the cover plate and said top circular plate by the weld connections or the thread connections with the compression fittings or the fittings with the O-rings;
(xviii) sealing threaded vent hole in the cover plate by a vent plug with the compression fittings or the fittings with the O-rings in between;
(xix) the threaded hole for a fluid hose/pipe in the top of the cover plate to be provided with a male end with the compression fitting or the fitting with the O-rings;
(xx) prior to performing the test, connecting a fluid hose/pipe beginning from a control panel to the threaded hole for fluid hose pipe in the cover plate.

2. The method for determining the horizontal stress versus the radial strain relationship using the Pressuremeter Probe in accordance with claim 1, the method further comprising:
(i) In a first drilling method, drilling a test hole to the diameter equal to the diameter of the pressuremeter probe to a small distance below the bottom of test depth;
(ii) stabilizing the test hole by slurry in subsurface conditions prone to caving during drilling or during performing the test;
(iii) filling the pressuremeter probe with fluid slowly till fluid comes out of the vent pipe with no air bubbles, after which the vent pipe to be closed by the vent plug;
(iv) setting the pressuremeter probe over the test hole and pushing it into the test hole under downward force of a drill rig to the test depth for performing the test;
(v) performing the pressuremeter test in pressure increments and recording readings for each pressure increments along with corresponding increase in volume of fluid inside the membrane or increase in radial displacement/expansion of the membrane and holding each pressure increment up to a selected time interval;
(vi) or performing the pressuremeter test in volume increments and recording the readings for each volume increments along with the corresponding increase in the pressure of fluid inside the membrane or the increase in the radial displacement/expansion of the membrane and holding each volume increment up to the selected time interval;
(vii) after completion of the test, decreasing the pressure in several decrements to zero value and then withdrawing the pressuremeter probe out of the ground or pushing it to next test depth to perform another pressuremeter test;
(viii) after withdrawing the pressuremeter probe out of the ground, drilling the test hole to another test depth and preparing the pressuremeter probe for next test depth;
(ix) in second drilling method, first drilling the test hole to the diameter about equal to the a diameter of the pressuremeter probe up to a depth where top of the pressuremeter will be seated;
(x) preparing the pressuremeter probe to perform the test;
(xi) lowering down the pressuremeter probe in the test hole till the bottom of the pressuremeter probe is seated at the top of the test depth where the test hole's diameter begins to be less than the diameter of the pressuremeter probe;
(xii) pushing the pressuremeter probe by applying downward vertical force taking reaction from the drill rig or a CPT rig or a moveable loaded box/platform or a platform with anchors/piles while the cutter ring scraping/cutting the test hole walls to diameter equal to the diameter of the pressuremeter probe up to or below the bottom of the test depth;
(xiii) performing the pressuremeter test in the pressure increments and recording the readings for each pressure increments along with the corresponding increase in the volume of fluid inside the membrane or the increase in the radial displacement/expansion of the membrane and holding each pressure increments up to the selected time interval;
(xiv) or performing the pressuremeter test in the volume increments and recording the readings for each volume increments along with the corresponding increase in the pressure of fluid inside the membrane or the increase in the radial displacement/expansion of the membrane and holding each volume increments up to the selected time interval;
(xv) after the completion of the test, decreasing the pressure or volume in the selected decrements to zero value;
(xvi) withdrawing the pressuremeter probe out of the ground;
(xvii) preparing the pressuremeter probe for the next test depth/depths in accordance with the specification or drawings using the same procedure as used for the first test;

(xviii) for measurements of the increase of the volume of the fluid inside the membrane, using either measurements from read-out unit in the control panel or measurements from counter of a mechanical actuator;

(xix) or calculating in the increase of the volume of the fluid inside the membrane by measuring the radial displacement/expansion by strain arms, mounted at the mid-height of the expanding section of the pressuremeter;

(xx) measuring the fluid pressure either from the read-out unit in the control panel or from strain gaged cell mounted within the expanding section of the pressuremeter.

3. The method for determining the horizontal stress versus the radial strain relationship using the Pressuremeter Probe in accordance with claim 2, the method further comprising:

(i) in a third drilling method, the pressuremeter probe is provided with an auger/drill bit to self-bore the test hole;

(ii) for this method, attaching a first pipe at the center of the pressuremeter probe between upper and lower circular plates and then inserting a second pipe inside the first pipe;

(iii) after having inserted the second pipe inside the first pipe to below the lower circular plate attached to a bottom end of the porous tube, attaching the auger/drill bit to the second pipe to self-bore the test hole;

(iv) providing the fluid pipe on left side of the center and the vent pipe on right side of the center of the pressuremeter probe or vice versa;

(v) all other details for the expandable jacket, the membrane, the porous tube, the guard cell and the cutter ring and their attachments remain the same as described for the first and the second drilling methods;

(vi) using the same procedure for performing the pressuremeter test for the third method as explained for the first and the second drilling methods;

(vii) performing the pressuremeter tests using a self-boring pressuremeter test method, continuously one after the other, without withdrawing the pressuremeter probe out of the ground, unless it becomes necessary due to unforeseen circumstances such as bursting of the membrane.

4. The method for determining the horizontal stress versus the radial strain relationship using the Pressuremeter Test Probe in accordance with claim 3, the method comprising:

(i) for the third drilling method, a drill bit with axial injection of prepared drilling mud/slurry to be used to stabilize the hole for the soils prone to caving during drilling or performing the pressuremeter or the self-boring pressuremeter test;

(ii) for this drilling method, generally using a three-wing bit for clays, silts and fine sands and a roller bit for gravelly soils.

5. The method for determining the horizontal stress versus the radial strain relationship using the Pressuremeter Probe in accordance with claim 2, the method further comprising:

(i) For the first and the second drilling methods, a drill bit with axial injection of preparing prepared drilling mud/slurry to be used to stabilize the hole for the subsurface soils prone to caving during drilling or performing the pressuremeter or the self-boring pressuremeter test;

(ii) for both drilling methods, generally using a three-wing bit for clays, silts and fine sands and a roller bit for gravelly soils.

6. A method for determining horizontal stress versus radial strain relationship using a Pressuremeter Probe, the method comprising:

(i) the pressuremeter probe comprising an expandable jacket for determining the horizontal stress versus the radial strain relationship for subsurface rocks;

(ii) the expandable jacket comprising two layers of circular arch shaped segmented plates and bands or rings, which are expandable;

(iii) first layer comprising a plurality of the circular arch shaped segmented plates, named as loading circular arch shaped segmented plates, which surround and in contact with a plurality of hydraulic jack assemblies, spaced vertically in the pressuremeter probe;

(iv) second layer comprising a plurality of the circular arch shaped segmented plates surrounding and in contact with the loading circular arch shaped segmented plates;

(v) the bands or rings surrounding the second layer of the circular arch shaped segmented plates;

(vi) staggering the second layer of the circular arch shaped segmented plates on the first layer of the loading circular arch shaped segmented plates, such that the load applied by hydraulic jacks are equally distributed on to the second layer of the circular arch shaped segmented plates, which in turn equally distributes load on test hole walls;

(vii) installing the bands or rings around circular or rectangular grooves in the second layer of the circular arch shaped segmented plates, such that the bands or rings remain flush with outside surface of the circular arch shaped segmented plates;

(viii) installing two O-rings in the circular or rectangular grooves of a top circular plate above the circular arch shaped segmented plates and the two O-rings in the circular or the rectangular grooves of a bottom circular plate below the circular arch shaped segmented plates, such that one of the two O-rings remain in contact with bottom and top ends of the loading circular arch shaped segmented plates and other one of the two remain in contact with the bottom and the top ends of the second layer of the circular arch shaped segmented plates in order to prevent any infiltration of rock fragments into the pressuremeter probe;

(ix) installing a fluid pipe in between the top and the bottom circular plates to let hydraulic fluid flow to hydraulic jack cylinders through holes provided in the fluid pipe;

(x) during pumping the hydraulic fluid with the help of a hydraulic pump, pressurized hydraulic fluid flowing in the fluid pipe and then through the holes in the fluid pipe, flowing in to hydraulic jack cylinders, pushing pistons move forward to radially displace the two layers of the circular arch shaped segmented plates and then radially displacing the test hole walls, while applying equally distributed load on the test hole walls;

(xi) attaching the fluid pipe to the top and the bottom circular plates by either weld connection or threaded connection with compression fittings or fittings with the O-rings;

(xii) providing a threaded circular hole in the center of the top circular plate to attach the fluid pipe or fluid hose to connect to the hydraulic pump located at ground surface;

(xiii) using the compression fittings or the fittings with the O-rings for the threaded connections to connect the fluid pipe to the top and bottom plates and to connect the fluid pipe/hose to the top plate;

(xiv) providing a threaded circular groove in the top plate to attach drill rods;

(xv) using drill rods to lower down the pressuremeter probe into a test hole to the test depth or to pull out the pressuremeter probe out of the ground after completion of the tests;

(xvi) size of the test hole is equal or very slightly greater than the diameter of the pressuremeter probe, so that the pressuremeter probe when inserted in the test hole touches the test hole walls and smoothly enters in the test hole.

7. The method for determining the horizontal stress versus the radial strain relationship using the Pressuremeter Test Probe in accordance with claim 6, the method comprising:

(i) for measurement of radial displacement/expansion of the two layers of the circular arch shaped segmented plates, installing LVDTs in the hydraulic jacks located at mid-height of expanding test section of the pressuremeter;

(ii) measuring hydraulic pressure created by the hydraulic pump inside the hydraulic jacks by a pressure gage.

8. A method for determining horizontal stress versus radial strain relationship using a Pressuremeter Probe, the method comprising:

(i) the pressuremeter probe comprising an expandable jacket surrounding and in contact with a hydraulic jack assembly, for determining the horizontal stress versus the radial strain relationship for subsurface soils, and intermediate geomaterials;

(ii) the expandable jacket comprising two layers of circular arch shaped segmented plates and bands or rings, which are expandable;

(iii) first layer comprising a plurality of the circular arch shaped segmented plates, named as loading circular arch shaped segmented plates, which surround and in contact with a plurality of hydraulic jack assemblies, spaced vertically in the pressuremeter probe;

(iv) second layer comprising a plurality of the circular arch shaped segmented plates surrounding and in contact with the loading circular arch shaped segmented plates;

(v) the bands or rings surrounding the second layer of the circular arch shaped segmented plates;

(vi) staggering the second layer of the circular arch shaped segmented plates on the first layer of the loading circular arch shaped segmented plates, such that the load applied by hydraulic jacks are equally distributed on to the second layer of the circular arch shaped segmented plates, which in turn applying equally distributed load on test hole walls;

(vii) installing the bands or rings in and around circular or rectangular grooves in the second layer of circular arch shaped segmented plates, such that the bands or rings remain flush with outside surface of the second layer of the circular arch shaped segmented plates;

(viii) installing two O-rings in the circular or rectangular grooves of top circular plate above the circular arch shaped segmented plates and the two O-rings in the circular or rectangular grooves of bottom circular plate below the circular arch shaped segmented plates, such that one of the two O-rings remain in contact with bottom and top ends of loading circular arch shaped segmented plates and other one of the two remain in contact with the bottom and top ends of the second layer of the circular arch shaped segmented plates in order to prevent any infiltration of rock fragments into the pressuremeter probe;

(ix) installing a fluid pipe in between the top and the bottom circular plates to let hydraulic fluid flow to hydraulic jack cylinders through holes provided in the fluid pipe;

(x) during pumping the hydraulic fluid with the help of hydraulic pump, pressurized hydraulic fluid flows in the fluid pipe and then through the holes in the fluid pipe, fluid flows in to the hydraulic cylinder;

(xi) which in turn, pushing pistons to move forward to radially displace the two layers of the circular arch shaped segmented plates and then radially displacing the test hole walls by applying equally distributed load on the test hole walls;

(xii) attaching the fluid pipe between the top and bottom circular plates by either weld connection or threaded connection with compression fittings or fittings with the O-rings;

(xiii) providing a threaded circular hole in the center of cover plate to attach the fluid pipe or fluid hose which connects to hydraulic pump at the ground surface;

(xiv) using the compression fittings or the fittings with O-rings connecting the fluid pipe between the cover and the top circular plates located vertically below the fluid pipe/hose attached at the top of the cover plate to lead to the hydraulic pump at the ground surface;

(xv) designing thickness of the two layers of the circular arch shaped segmented plates and the fluid pipe in order for them to remain vertical with the lateral support provided by the bands or rings;

(xvi) providing a guard cell comprising of a circular tube/pipe, thread connected or weld connected to the top circular plate located above the two layers of the circular arch shaped segmented plates;

(xvii) providing a cutter ring comprising of the circular tube/pipe, the top end of which thread connected or weld connected to the bottom circular plate located below the two layers of the circular arch shaped segmented plates;

(xviii) the bottom end of the cutter ring having a knife edge in order to scrap/cut the test hole walls to the size of the pressure meter probe;

(xix) the guard cell covered by a cover plate;

(xx) attaching the top of the guard cell to the cover plate by the weld or the thread connection;

(xxi) the threaded hole for the fluid pipe/hose in the cover plate to be provided by the compression fittings or the fittings with O-rings with a male end screwed in to the top of the threaded hole for the fluid pipe and the other end of the compression fitting provided with a tube fitting;

(xxii) providing a threaded circular groove in the top plate to attach drill rods;

(xxiii) using the drill rods to lower down the pressuremeter probe into a test hole at the test depth or to pull out the pressuremeter probe out of the ground after completion of the tests;

(xxiv) this pressuremeter probe which uses the hydraulic jacks shall also be used to determine lateral stress versus radial strain relationship for weak rocks, shales and jointed weak rock rocks.

9. The method for determining the horizontal stress versus the radial strain relationship using the Pressuremeter Probe in accordance with claim 8, the method comprising:

(i) using two drilling methods for making the test hole;

(ii) in first drilling method, drilling the test hole to a diameter equal to the diameter of pressuremeter probe to a small distance below the bottom of test depth;
(iii) stabilizing the test hole during drilling by slurry;
(iv) setting the pressuremeter probe over the test hole and pushing it into the test hole under downward force of a drill rig to the test depth for performing the test;
(v) performing the pressuremeter test in pressure increments and recording readings of the pressure increments and increase in radial displacement/expansion of the two layers of the circular arch shaped segmented plates and holding each pressure increment to a selected time interval;
(vi) after completion of the test, decreasing the pressure in selected decrements to zero value and then withdrawing the pressuremeter probe out of the ground or pushing it to next test depth to perform another pressuremeter test;
(vii) in second test method, first drilling the test hole to the diameter about equal to the diameter of the pressuremeter probe up to a depth where bottom of pressuremeter probe will be seated;
(viii) preparing the pressuremeter probe to perform the test;
(ix) lowering down the pressuremeter probe in the test hole till the bottom of the pressuremeter probe is seated at the top of the test depth where the test hole's diameter begins less than the diameter of the pressuremeter probe;
(x) pushing the pressuremeter probe by applying downward vertical force taking reaction from drill rig or CPT rig or moveable loaded box/platform or a platform with anchors/piles while cutter ring scraping/cutting the test hole walls to diameter equal to the diameter of the pressuremeter probe up to the bottom of the test depth;
(xi) performing the pressuremeter test in selected pressure increments and taking and recording readings of pressure increments and increase in radial displacement/expansion of the two layers of the circular arch shaped segmented plates by holding each pressure increment to a selected time interval;
(xii) after completion of test, decreasing the pressure in selected increments to zero value;
(xiii) repeating the same procedure to perform next test/tests;
(xiv) for measurement of the radial displacement/expansion of the two layers of the circular arch shaped segmented plates, installing LVDTs in the hydraulic jacks located at mid-height of expanding test section of the pressuremeter;
(xv) measuring hydraulic pressure created by the hydraulic pump inside the hydraulic jacks by a pressure gage.

10. The method for determining the horizontal stress versus the radial strain relationship using the Pressuremeter Test Probe in accordance with claim 8, the method comprising:
(i) for the first and the second drilling methods, a drill bit with axial injection of prepared drilling mud/slurry to be used to stabilize the hole for the soils prone to caving during drilling or performing the pressuremeter or the self-boring pressuremeter test;
(ii) for both drilling methods, generally using a three-wing bit for clays, silts and fine sands and a roller bit for gravelly soils.

* * * * *